US006664039B1

(12) United States Patent
Benzer et al.

(10) Patent No.: US 6,664,039 B1
(45) Date of Patent: Dec. 16, 2003

(54) METHODS AND COMPOSITIONS FOR MODULATING NEURODEGENERATION

(75) Inventors: Seymour Benzer, San Marino, CA (US); Kyung-Tai Min, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/418,963

(22) Filed: Oct. 14, 1999

Related U.S. Application Data
(60) Provisional application No. 60/104,298, filed on Oct. 14, 1998.

(51) Int. Cl.[7] .............................. C12Q 1/00; C12N 9/00; C12N 9/99
(52) U.S. Cl. .............................. 435/4; 435/183; 435/184
(58) Field of Search .................... 530/350; 435/183, 435/4, 7.1

(56) References Cited

PUBLICATIONS

Kyung–Tai Min et al., "Spongecake and eggroll: two heredity diseases in Drosophila resemble patterns of human brain degeneration", *Curr. Biol.*, 7:885–888 (1997).

Jean Mosser et al., "Putative X–linked adrenoleukodystrophy gene shares unexpected homology wit ABC transporters," *Nature*, 361:726–730 (1993).

Natalie Cartier et al., "Retroviral–mediated gene transfer corrects very–long–chain fatty acid metabolism in adrenoleukodystrophy fibroblasts," *Proc. Natl. Acad. Sci. USA*, 92:1674–1678 (1995).

Takuro Kobayashi et al., "Adrenoleukodystrophy Protein–Deficient Mice Represent Abnormality of Very Long Chain Fatty Acid Metabolism," *Biochem. Biophys. Res. Commun.*, 232:631 (1997).

Sonja Forss–Petter et al., "Targeted Inactivation of the X–Linked Adrenoleukodystrophy Gene in Mice," *Journal of Neuroscience Research*, 50:829–843 (1997).

*Primary Examiner*—Anne-Marie Falk
(74) *Attorney, Agent, or Firm*—Fish & Richardson P.C.

(57) ABSTRACT

Disclosed are polypeptides and polynucleotides having very long chain fatty acid coA synthetase activity. The polypeptides and polynucleotides are useful in identifying and modulating neurodegeneration.

7 Claims, 10 Drawing Sheets

CTGAATTCGTCGTGTTTGCTGTCGTGGTTCTCGAGCGAAAGAAAGAGTGGGAGTATAGAAA
ATAGACGGCAATCGATTTGCGTGACCAAGAACAAATATATACATACATATATCGAGAACGC
CGTAGAAACACCAAACTAGTTAATTATCCTTGCAACATGTCCACGATAGACGCGCTCTACAAT
CGTCCTGGGCCCAACCCGCCTGCGCCAGGCGGATGCCTATCGCACCACCAATCGTCAGGAT
GCCGTCAAGATTCGTATGCCAAGGATCGGAATCGGCGCAGAGAGCCCATCTCCGTGCCC
GGCCTGCTGAAGCGTACGGTCAACACTGTCACCTACACAAACAATATGGCGACTATCCTGCGCTGCCACCAAGAACG
GCAAGAACGGATATCACACTGTCACCTACACAAACAATATGAGCAGAAGGTGCACCAGGTGGC
CAAGGCGTTCATTAAGCTCGGTCTGGAGGAGCACCATTCGGTGGGTGTGCTGGCCTTCAAT
TGCGCCGAATGGTTCTACTCCGCCGATGCAGCACGTTCTGGAGAGCTCACATGCCCAAAT
TCTACACCACCAATTCCGCCAATCGACCTGCAGCACGTTCTGGAGAGCTCACATGCCCAAAT
CGTGGTCGTCGACGACGCCAAGCACCATTCAGATCGCCATTCGCGACAAGCTGCCC
AAGCTCAAGGCCCGCCATTCAGATCGAGTCAACGAGTGCTGTCTACACCTCCGAACG
GCTACTACAGGTGGTCGGAGAATGTGGCGATCGAGTGCTGTCTACACCTCCGAACG
GACCCGTTTGGAGAATGTGGCGATCAACGAGTGCTCCCACGACAACATCACCTTCGATGTGCGGCA
GTGGGCATGCCAAGGGCGTGATGCTCTCCCACGACAACATCACCTTCGATGTGCGGCA
TCGTCAAGGCCATGGACCGTGGACCGTGGACATTTACACCTGGGCCCTTGTGGGCTGCATT
TTCGCACGTGGCCCGCCCAGACCGTGGACATTACACCTGCTGGTGCAGGATGCGCGA
TGGTTCGCCGACAAGGATCATGGGCGTGCCGCTGAAGTCGTTGCAGGATGCGCGA
CCCACGCGATTCATGGGCGCGGCCAGCCTGCAGCCCAGCCTGGGCCAAGGGCATCACG
GTGCCAGCGCTCAGCACTGTGAGTGAAGGCAAGAGCTCGCCAGCTGGGCCAAGGGCATCACG
CTGAAGCACTACATGTGAGTGAAGGCAAGAGCTCGCCAGCTGGGATTCCGTACAAGATTGCCA
AGTCGCTCATCATGTCCAAGGTGAAGCAGGCCCCTGGGCTTCGATCGCGTCCTTACACTGGC
CAGTGCGGCAGCCTCCCATGCGGCATGTCAGACGAAGAGTACTTCCTCAGTCTGACCTAAAG
ATTGTCGATGCCTTCGACACATCGGCATGTCAGAATCGGCCGGTTGTCACACATCTGCCTTCCCGATTC
CGTGGGTCTGAACACAATCGGCAAAACTTTGCCCGGCTGCGAGTCCAAGTTCATTCAACAAG

FIG. 3A-1

```
GATGCCAACGGTCACGGAGAGCTGTGCATCCGAGGAGCGTCACGTTTCATGGCTACATCG
ACAACAAGGAGAAGACCGAGGAGTCGCTGCTGGATGACGACTGCTGGCATTCCGGTGATTT
GGGATTTGTGGATGACAAGGGTTATGTTTCACTGACGGACGATCCAAGGAGATCATCATTA
CCGCGGCGGCGAGAACATACCGCCAGTGCACATCGAGAACACGATCAAGAAGGAAGCTGG
ATGCCATTTCCAATGCCTTTTTGGTGGGCGAGCAGCGCAAATATCTCACTGTTCTGATCACC
CTAAAGACCGAAGTGGACAAGGATTCCGGTGAGCCGCGTGAGCGCTTAGCCACGAGTCCT
CCGTGTGGGTGAAATCGCTGGGAGTGGAGCACAAGACCGTATCGGATATCCTGGCCGCAG
GTCCCTGCCCCAAGGTGTGGAAGTTCAGAAGTTCACCATTCTGCCGCACGACTTCTCCATTCCCA
CATTTCCAATGCCCAAAAGTTAAGCCTAAAGGTTAAGCGCAACGTTGTGTCCAAGATGTATG
CCGGCGAACTTGGACCACCCACCTATATGTCCTAGATTTCTCACTGCAAGATCGAAAACCGATGATAGC
CCGATGAGATCGAGAAACTGAGCTTTAATGTGAATTTGAATTTAACGGAGACTTCCAAGCCAATTGAGTGCCA
CGCGGAACTTGAGCTTTGATTTAGGCTGATGTTAACTGTTGGATATTAAACTAAGAACAACTATGGCCCTA
CTTTTAATTTGATTTAGGCTAGACACGAGCTTGCCAACGATTAGGTCCAGAGATCATTAATTAGTAACTAAG
TGCCTAGGTAGACACGAGCTTGCCAACGATTAGGTTGTTACCAACTGGTTGTACCAACTGAACAAACGAAAATTGTTTATTGTCTGAAG
TTTTATTTTTATATACTATTTGGTTGTACCAACTGAACAAACGAAAATTGTTTATTGTCTGAAG
AGCAACAATAAATTTGTAATTAGATTAACTACCAAAAAAAAAAAAAAA
```

FIG. 3A-2

```
CTGAATTCGGTCGTCGTGTTGCTGCTGGTTCTCGAGCGAAAGAAGAGTGGGAGTATAGAAAATAGACGGCA
ATCGATTTGCCGTGACCAAAGAACAAATATATACATACATATATCGAGAAACGCCGTAGAAACCAAACTAGTTA
ATTATCCTTGCAACMSTIDALYNRPGPNRLRQADAYRTTNRQDAVKIRMAKDGIGAEEPISVPGL
LKRTVNNYGDYPALRTKNGKNGYHTVTYKQYEQKVHQVAKAFIKLGLEEHHSVGVLAFNCA
EWFYSAMGAIHARGIIAGIYTTNSADAVQHVLESSHAQIVVVDDAKQMDKIHAIRDKLPKLKA
AIQIQEPYSPYLKKEDGYYRWSEIESMNVSDVEDQYMTRLENVAINECCCLVYTSGTVGMPK
GVMLSHDNITFDVRGIVKAMDRVVVGAESIVSYLPLSHVAAQTVDIYTCAFVAGCIWFADKDA
LKGTLVKSLQDARPTRFMGVPRVYEKFQERMVAVASSSGSLKKMLASWAKGITLKHYMVS
QGKSSGGFRYKIAKSLIMSKVKQALGFDRVLTLASAAAPMSPETKKYFLSLDLKIVDAFGMS
ETAGCHTICLPDSVGLNTIGKTLPGCESKFINKDANGHGELCIRGRHVFMGYIDNKEKTEESL
DDDCWLHSGDLGFVDDKGYVSLTGRSKEIIITAGGENIPPVHIENTIKKELDAISNAFLVGEQR
KYLTVLITLKTEVDKDSGEPLDELSHESSVWVKSLGVEHKTVSDILAAGPCPKVWKSIEDAIK
RANKQSISNAQKVQKFTILPHDFSIPTGELGPTHPKG*CGGACTTCCAAGCCAATTGAGTGCCACTTT
TAATTTGATTTAGGCTGATGTTAACTGTTGGATATTAACTGTTAAACTAAGAACAACTAAGAACAACTATGCCCTATGCCTAGGTAGACA
CGAGCTTGCCAACGATTAGGTCCAGAGATCATTAATTAGTAACTAAGTTTTATTTTTATATACTATTGGTTG
TACCAACTGAACGAAAATTGTTTATTGTCTGAAGAGCAACAATAAATTGTAATTAGATTAACTACCAAAA
AAAAAAAAAAAA
```

B = Bubblegum
H = Human KIAA0631
R = Rat VLCFA Synth.

```
             360       370       380       390       400       410       420
B  LKKMLASWAKGITLKHYMVSQKKSSGGFRYKIAKSLIMSKVKQALGFDRVLTLASAAAPMSPETKKYFLS
H  IRRKMLIWAMSVTLEQNLTCPGSDLKPFTTRLADYLVLAKVRQALGFAKCQKNFYGAAPMAETQHFFLG
R  VKIALGNGLRGDVWREFIKRFG------DIHIYFYASTEGNIGFMNYPRKIGAVG-----RENYLQK 430       440       450       460       470       480       490
B  LDLKIVDAFGMSETAGCTICLPDSVGLNTIGKTTLPGCESKEINKDANGHGELCIRGRHVFMGYIDNKEK
H  LNIRLYAGYGLSETSGPHFMSSPYNYRLYSSKLVPGCRVKLVNQDAEGIGEICLWGRTIFMGYLNMEDK
R  KVVRHELIKYDVKEDEPVRDANGYCIKVP----K-GEVGLLICKITELTPFFGYAG-----GKTQTEKK 500       510       520       530       540       550       560
B  TEESLDDDC---WLHSGDLGFVDDKGYVSLTGRSKEIITAGGENIPPVHIENTI-----KKELDAISNAFL
H  ICEAIDEEG---WLHTGDAGRLDADGFLYITGRLKELIITAGGENVPPVPIEEAV----KMELPIISNAMI
R  KLRDVFKKGDVYFNSGDLLMIDRENFIYFHDRVGDTFRWKG-ENVATTEVADIVGLVDFVEVNVYGVEV 570       580       590       600       610       620       630
B  VGEQRKYLTVLITLKTEVDKDSGEPIDELSHESSVWKSLGVEHKTVSDILAAGPCPKVWKSIEDAIKRA
H  IGDQRKFLSMLLTLKCTLDPDTSDQTDNLTEQAVEFCORVGSRATTVSEIIEK-KDEAVYQAIEEGIRRV
R  PGHEGRIGMASJKMKENYEFNGKKLFQHISEYLPSYSRPFLRIQDTIEIFGT--FKHRKVTLMEEGFNPS 640       650       660       670       680       690       700
B  NKQSISNAQKVQKFTILPHDFSIPTGELGPTHPKG
H  NMNAAARPYHIQKWAIIERDESISGGELGPTMKLKRLTVLEKYKGIIDSFYQEQKM
R  VLKDTLYFMDDTEKIYVPMTEDIYNAIIDKTLKL
```

METHODS AND COMPOSITIONS FOR MODULATING NEURODEGENERATION

CROSS REFERENCE TO RELATED APPLICATIONS

This application claims priority from U.S. Provisional Application Serial No. 60/104,298, filed Oct. 14, 1998, to which application a priority claim is made under 35 U.S.C. §119(e).

The U.S. Government has certain rights in this invention pursuant to Grant Nos. AG12289 and EY09278 awarded by the National Institute of Health.

FIELD OF THE INVENTION

This invention relates to newly identified polynucleotides, polypeptides encoded by such polynucleotides, the use of such polynucleotides and polypeptides, as well as the production and isolation of such polynucleotides and polypeptides. More particularly, methods and compositions useful in modulating neurodegeneration are provided.

BACKGROUND OF THE INVENTION

Drosophila, with its short generation time, highly evolved nervous system, and amenability to genetic and molecular techniques, may be a useful model system for understanding neurodegenerative diseases and for development of methods for prevention and treatment. For instance, the mutants, drop-dead (Benzer, S., *J. Am. Med. Assn.* 218:1015–1022 (1971)), and swiss cheese (Kretzschmar et al., *Neuroscience*, 17:7425–7432 (1997)) show late-onset degeneration in the adult brain; spongecake and eggroll (Min and Benzer, *Curr. Biol.*, 7:885–888 (1997)) exhibit brain degeneration patterns similar to those seen in human diseases. Adrenoleukodystrophy (ALD) in humans is manifested by gradual neurological deterioration with demyelination, blindness and early death. In a milder form, referred to as adrenomyeloneuropathy, which involves mutations in the same gene, there is later onset, with progressive paraparesis and distal axonopathy (Moser, H. W., *Brain*, 120:1485–1508 (1997)). The gene associated with ALD, has been identified as a member of the ATP-binding cassette (ABC) transmembrane transporter superfamily and may be needed for the transport of very long chain fatty acid acyl (VLCFA) CoA synthetase (Mosser et al., *Nature*, 361:726–730 (1993)) resulting in decreased affinity of VLCFA-CoA synthase. The deficiency in activity of the synthetase, which normally metabolizes the VLCFAs, causes elevated levels of hexacosanoic acid (C26:0) in serum (Moser, supra). Transfer of the normal cDNA for the ATP-binding cassette transmembrane proteins into ALD fibroblasts can correct the C25 level (Cartier et al., *Proc. Natl. Acad. Sci. USA*, 92:1674–1678 (1995)).

In X-linked human ALD and in three knockout mice of the ABC transporter gene (Kobayashi et al., *Biochem Biophys. Res. Commun.* 232:631 (1997); Foiss-Peller et al., *J. Neurosci. Res.* 50:829 (1997)) there was no correlation between the amount of VLCFAs and the severity of pathology. Some individuals with high VLCFAs escaped the neurological defects and the knock out mice did not show the pathology of ALD in spite of having elevated VLCFAs. These observations suggest that excess VLCFAs and the pathology may not have a direct causal relationship, but may be separate ramifications of another, underlying defect.

SUMMARY OF THE INVENTION

In a first embodiment, the present invention provides a substantially purified very long chain fatty acid coA-synthetase (VLCFA coA-syn) polypeptide also referred to as "bubblegum" (BLG), having an amino acid sequence as set forth in SEQ ID NO:2.

In another embodiment, the present invention provides an isolated polynucleotide encoding an amino acid sequence as set forth in SEQ ID NO:2. The isolated polynucleotide is selected from the group consisting of SEQ ID NO:1; SEQ ID NO:1, wherein T can also be U; a nucleic acid sequence complementary to SEQ ID NO:1; and fragments thereof that are at least 15 bases in length and that hybridize under stringent conditions to DNA which encodes the polypeptide of SEQ ID NO:2.

In another embodiment, the present invention provides an expression vector containing a VLCFA coA-syn polynucleotide. The vector can be for example, a plasmid or a viral vector.

In yet another embodiment, the present invention provides a host cell transformed with an expression vector containing a VLCFA coA-syn polynucleotide.

In yet a further embodiment, the present invention provides a method of producing a VLCFA coA-syn polypeptide by transforming a host cell with a VLCFA coA-syn polynucleotide; expressing the polynucleotide in the host; and recovering the VLCFA coA-syn polypeptide.

In another embodiment, an antibody that binds to the polypeptide of SEQ ID NO:2 is provided. The antibody can be polyclonal or monoclonal.

The present invention also provides a method for identifying a compound which modulates VLCFA coA-syn expression or activity comprising: incubating components comprising the compound and a VLCFA coA-syn polypeptide, or a recombinant cell expressing a VLCFA coA-syn polypeptide, under conditions sufficient to allow the components to interact; and determining the effect of the compound on the expression or activity of the gene or polypeptide, respectively.

In yet another embodiment, the present invention provides a method of producing a non-human organism having an increased life span comprising: introducing a transgene disrupting or interfering with expression of very long chain fatty acid coA-synthetase (VLCFA coA-syn) into germ cells of a pronuclear embryo of the organism; implanting the embryo into the oviduct of a pseudopregnant female thereby allowing the embryo to mature to full term progeny; testing the progeny for presence of the transgene to identify transgene-positive progeny; and cross-breeding transgene-positive progeny to obtain further transgene-positive progeny.

In yet another embodiment, the present invention provides a transgenic organisms having a phenotype characterized by neurodegeneration. The organism may be any non-human organisms, including, for example, mammals (bovine, porcine) and invertebrates such as Drosophila.

These and other aspects of the present invention will be apparent to those of skill in the art from the teachings herein.

BRIEF DESCRIPTION OF THE DRAWINGS

The following figures are examples of embodiments and are not meant to limit the scope of the invention.

FIGS. 3A1 and 3A2 shows the bubblegum polynucleotide sequence. FIG. 3A3 shows a polynucleotide and polypeptide sequence of bubblegum VLCFA acyl CoA synthetase. FIGS. 3B1 and 3B2 show an alignment with rat VLCFA acyl CoA synthetase and a human sequence. Identical and similar amino acids are identified as boxes.

DETAILED DESCRIPTION OF THE INVENTION

The present invention provides polypeptides and polynucleotides encoding the polypeptides, wherein each polypeptide is characterized as a neurodegenerative related polypeptide having very long chain fatty acid coA-synthetase activity.

Figure 2A:
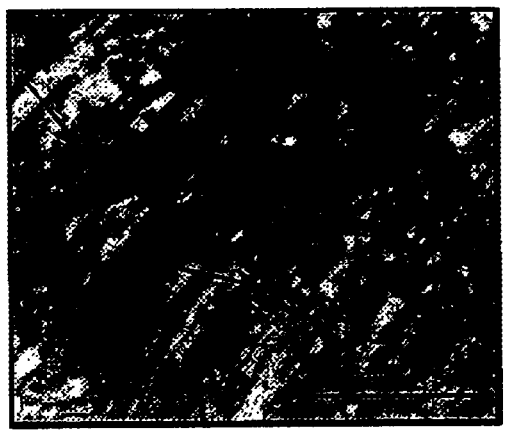
FIGS. 2A–D shows unstructural abnormalities in the bubblegum mutant. (A) shows the lamina of one day old bubblegum mutant fly. The photoreceptor axons (arrows), are normal in diameter (indicated by brackets). (B) In a 15 day old bubblegum, photoreceptor axons are greatly expanded. (C) tangential section of lamina of one day old bubblegum mutant shows the normal clustered array of second order axons surrounded by photoreceptor axons. (D) Fifteen day old bubblegum at the same magnification, showing the greatly dilated structure. Inset; tubulovesicular structures within photoreceptor axons (inset; scale bar: 0.5 µm). L, laminar second order axon; Pr, photoreceptor axon. Scale bar: 2 µm.
Figure 2B:
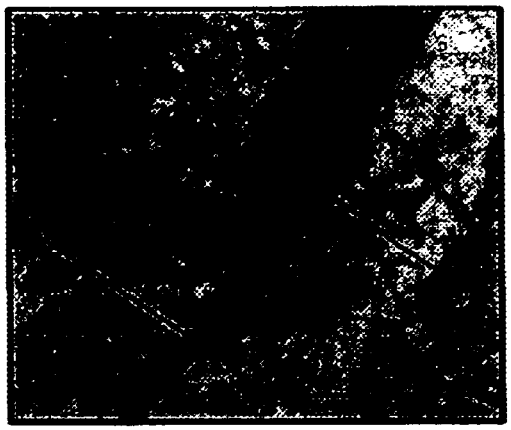
Figure 2C:
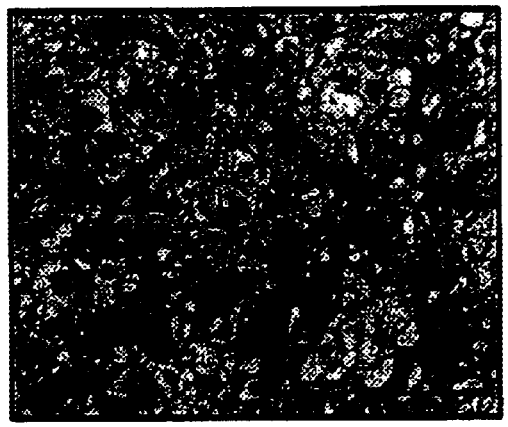
Figure 2D:
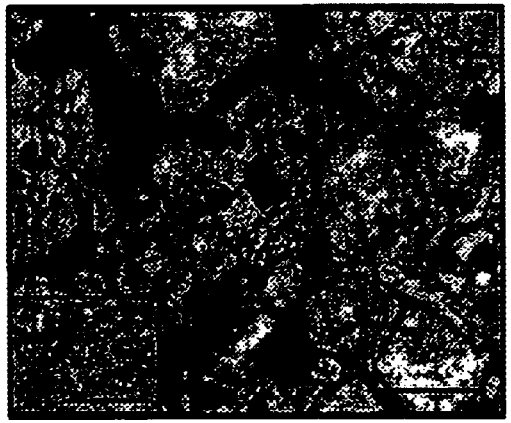

The VLCFA CoA-syn has also been termed a bubblegum polypeptide based upon the appearance of the mutant lamina in Drosophila. In the lamina (the equivalent in the fly of the ganglion cell layer in the vertebrate eye), photoreceptor axons entering from the retina form multiple synapses with a pair of monopolar, second order neurons. The photoreceptor axons are readily identified by the presence of capitate projections which, in sections, resemble golf balls on tees; these project in from surrounding glial sheaths. As shown in FIG. 2, with age, there is a great expansion of the photoreceptor axons and other structures, whereas the capitate projections remain normal in size. At high magnification, one can see an accumulation of tubulo-vesicular structures in the expanded axons (FIG. 2d. inset). These resemble the material that accumulates in vertebrate cerebral white matter after vinblastine treatment, which causes the destruction of microtubules (Hirano A., *A guide to Neuropathology*, Igaku-Shoin, New York, Tokyo, 1981).

VLCFA acyl CoA synthetase plays an important role in ALD. VLCFAs must be activated to their thioester derivatives by the enzyme before β-oxidation in peroxisomes. Reduced activity of the enzyme results in accumulation of VLCFA, especially C26. However, ALD patients currently have been identified as having mutations not of the VLCFA acyl CoA enzyme, but in a member of the ABC transporter superfamily (Mosser et al., *Nature*, 361:726 (1993)).

In ALD, dietary treatment has been used in an attempt to prevent progression of the disease by restoring the normal levels of VLCFAs. Feeding a monounsaturated fatty acid, glyceryl trioleate (GTO) oil, reduced the level of C26 in plasm by about 50% within 4 months (Rizzo et al., *Neurology*, 36:357–361 (1986); Moser et al., *Ann. Neurol.* 21:240–249 (1987)). So called "Lorenzo's oil", a combination of GTO and glyceryl trierucate, normalized the C26 accumulation in a month. These monounsaturated fatty acids are thought to compete in the fatty acid elongation system, reducing the levels of VLCFAs.

Among ALD patients, the mutations in the ABC transporter are at various locations within the gene and the clinical phenotype varies greatly. Even within a single family, the disease can range from severe to asymptomatic; no relationship has been found between the expression level of the ABC protein or mutants thereof, and severity of the disease. In the study by Kok et al., there were two cases in which the patients were diagnosed clinically as ALD, and showed high levels of C26, yet had no detectable mutations in the ABC gene. Burdette et al., diagnosed a patient with neural disorders, retinal pigmentary degeneration, and high level of C26 as being due to a unique peroxisomal disorder, the clinical phenotype being between that of ALD and the Zellweger syndrome, which results from lack of peroxisome function. Three different knockouts of the gene in mice failed to show demyelination or paraparesis, although some VLCFAs accumulation was found in the tissues. It is thought that there may be redundancy of the ABC-ALD-associated protein in the mice. Alternatively, there may be one or more other genes involved in determination of onset and severity of the diseases. Autosomal modifiers that influence the degree of clinical phenotype in ALD have also been proposed.

The major biochemical change in the disease is the high level of accumulation of C26. The β-oxidation of VLCFAs is catalyzed in several steps by different enzymes in peroxisomes, VLCFA acyl CoA synthetase, acyl CoA oxidase, bifunctional enoyl-CoA hydratase/3-hydroxy acyl-CoA dehydratase, and β-ketothilase. Enzyme disorders in any step of the oxidation processes can result in elevated levels of VLCFAs, causing peroxisomal diseases. The mutant bubblegum (described herein) shows the phenotypes associated with defective VLCFA acyl CoA synthetase, including accumulation of C26, neurodegeneration, visual impairment, and reduced lifespan, similar to the effects of mutations in the ABC gene.

The inventors found that GTO treatment of the mutant flies prevented the onset of degeneration, concomitant with the VLCFAs level in males becoming normal. While dietary treatment with "Lorenzo's oil" in ALD reduces the level of C26, there has been relatively little success, so far, in preventing progression of the disease.

In one embodiment the present invention provides a method for optimizing the treatment of ALD and associated neurodegenerative diseases using the mutant bubblegum as a useful model system for rapidly screening food additives and drugs for positive effects, and to study the molecular mechanism involved in neuropathy caused by the unbalance in fatty acid metabolism. At the same time, the fly could be used to identify suppressor or enhancer genes that change the phenotype of bubblegum, providing information on interaction of the synthetase with other genes.

To facilitate further understanding of the invention, a number of terms are defined below.

The term "isolated" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. As part of or following isolation, a polynucleotide can be joined to other polynucleotides, such as for example DNAs, for mutagenesis studies, to form fusion proteins, and for propagation or expression of the polynucleotide in a host. The isolated polynucleotides, alone or joined to other polynucleotides, such as vectors, can be introduced into host cells, in culture or in whole organisms. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions which are not naturally occurring compositions) and, therein remain isolated polynucleotides or polypeptides within the meaning of that term as it is employed herein.

The term "oligonucleotide" as used herein is defined as a molecule comprised of two or more deoxyribonucleotides or ribonucleotides, preferably more than three, and usually more than ten. The exact size of an oligonucleotide will depend on many factors, including the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.*, 68:90–99; the phosphodiester method of Brown et al., 1979, *Method Enzymol.*, 68:109–151, the diethylphosphoramidite method of Beaucage et al., 1981, *Tetrahedron Lett.*, 22:1859–1862; the triester method of Matteucci et al., 1981, *J. Am. Chem. Soc.*, 103:3185–3191, or automated synthesis methods; and the solid support method of U.S. Pat. No. 4,458,066.

The term "plasmids" generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Polynucleotide" or "nucleic acid sequence" refers to a polymeric form of nucleotides at least 10 bases in length. By "isolated nucleic acid sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double stranded forms of DNA.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is mixture of single-and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

Nucleic acid sequences can be created which encode a fusion protein and can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

A nucleic acid sequence of the invention including, for example, a polynucleotide encoding a fusion protein, may be inserted into a recombinant expression vector. The term "recombinant expression vector" refers to a plasmid, virus or other vehicle known in the art that has been manipulated by insertion or incorporation of a nucleic acid sequences of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988), baculovirus-derived vectors for expression in insect cells, cauliflower mosaic virus, CaMV; tobacco mosaic virus, TMV. The nucleic acid sequences of the invention can also include a localization sequence to direct the indicator to particular cellular sites by fusion to appropriate organellar targeting signals or localized host proteins. For example, a polynucleotide encoding a localization sequence, or signal sequence, can be used as a repressor and thus can be ligated or fused at the 5' terminus of a polynucleotide encoding a polypeptide of the invention such that the localization or signal peptide is located at the amino terminal end of a resulting polynucleotide/polypeptide. The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., 1989, and *Current Protocols in Molecular Biology*, M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., *Molecular Cloning A Laboratory Manual*, Cold Spring Harbor Laboratory, N.Y., 1989).

Depending on the vector utilized, any of a number of suitable transcription and translation elements, including constitutive and inducible promoters, transcription enhancer elements, transcription terminators, etc. may be used in the expression vector (see, e.g., Bitter, et al., *Methods in Enzymology* 153:516–544, 1987). These elements are well known to one of skill in the art.

In yeast, a number of vectors containing constitutive or inducible promoters may be used. For a review see, Current Protocols in *Molecular Biology*, Vol. 2, Ed. Ausubel, et al., Greene Publish. Assoc. & Wiley Interscience, Ch. 13, 1988; Grant, et al., "Expression and Secretion Vectors for Yeast," in *Methods in Enzymology*, Eds. Wu & Grossman, 1987, Acad. Press, N.Y., Vol. 153, pp.516–544, 1987; Glover, *DNA Cloning, Vol. II*, IRL Press, Wash., D.C., Ch. 3, 1986; and Bitter, "Heterologous Gene Expression in Yeast," *Methods in Enzymology*, Eds. Berger & Kimmel, Acad. Press, N.Y., Vol. 152, pp. 673–684, 1987; and *The Molecular Biology of the Yeast Saccharomyces*, Eds. Strathern et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: *DNA Cloning Vol. 11, A Practical Approach*, Ed. D M Glover, IRL Press, Wash., D.C., 1986). Alternatively, vectors may be used which promote integration of foreign DNA sequences into the yeast chromosome.

An alternative expression system which could be used to express a protein of the invention is an insect system. In one such system, *Autographa californica* nuclear poly-hedrosis virus (AcNPV) is used as a vector to express foreign genes. The virus grows in *Spodoptera frugiperda* cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith, et al., *J. Viol.* 46:584, 1983; Smith, U.S. Pat. No. 4,215,051.

By "transformation" is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., a Very long chain fatty acid coA-synthetase polypeptide), or fragment thereof.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*), or may be a mammalian cell, including a human cell.

Eukaryotic systems, and mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the nucleic acid sequences encoding a fusion protein of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the Very long chain fatty acid coA-synthetase polypeptide in infected hosts (e.g., see Logan & Shenk, *Proc. Natl. Acad. Sci. USA*, 81:3655–3659, 1984). Alternatively, the vaccinia virus 7.5K promoter may be used. (e.g., see, Mackett, et al., *Proc. Natl. Acad. Sci. USA*, 79:7415–7419, 1982; Mackett, et al., *J. Virol.* 49:857–864, 1984; Panicali, et al., *Proc. Natl. Acad. Sci. USA* 79:4927–4931, 1982). Of particular interest are vectors based on bovine papilloma virus which have the ability to replicate as extrachromosomal elements (Sarver, et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the Very long chain fatty acid coA-synthetase gene in host cells (Cone & Mulligan, *Proc. Natl. Acad. Sci. USA*, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the cDNA encoding a fusion protein of the invention controlled by appropriate expression control elements (e.g., promoter, enhancer, sequences, transcription terminators, poly-adenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell*, 11:223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22:817, 1980) genes can be employed in tk$^-$, hgprt$^-$ or aprt$^-$ cells respectively. Also, antimetabolite resistance can be used as the basis of selection for dhfr, which confers resistance to methotrexate (Wigler, et al., *Proc. Natl. Acad. Sci. USA*, 77:3567, 1980; O'Hare, et al., *Proc. Natl. Acad. Sci. USA*, 8:1527, 1981); gpt, which confers resistance to mycophenolic acid (Mulligan & Berg, *Proc. Natl. Acad. Sci. USA*, 78:2072, 1981; neo, which confers resistance to the aminoglycoside G-418 (Colberre-Garapin, et al., *J. Mol. Biol.* 150:1, 1981); and hygro, which confers resistance to hygromycin (Santerre, et al., *Gene* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047, 1988); and ODC (ornithine decarboxylase) which confers resistance to the ornithine decarboxylase inhibitor, 2-(difluoro-methyl)-DL-ornithine, DFMO (McConlogue L., In: *Current Communications in Molecular Biology*, Cold Spring Harbor Laboratory, ed., 1987).

The term "primer" as used herein refers to an oligonucleotide, whether natural or synthetic, which is capable of acting as a point of initiation of synthesis when placed under conditions in which primer extension is initiated or possible. Synthesis of a primer extension product which is complementary to a nucleic acid strand is initiated in the presence of nucleoside triphosphates and a polymerase in an appropriate buffer at a suitable temperature. The term "primer" may refer to more than one primer, particularly in the case where there is some ambiguity in the information regarding one or both ends of the target region to be synthesized. For instance, if a nucleic acid sequence is inferred from a protein sequence, a "primer" generated to synthesize nucleic acid sequence encoding the protein sequence is actually a collection of primer oligonucleotides containing sequences representing all possible codon variations based on the degeneracy of the genetic code. One or more of the primers in this collection will be homologous with the end of the target sequence. Likewise, if a "conserved" region shows significant levels of polymorphism in a population, mixtures of primers can be prepared that will amplify adjacent sequences. For example, primers can be synthesized based upon the amino acid sequence as set forth in SEQ ID NO:2 and can be designed based upon the degeneracy of the genetic code.

The term "gene" means the segment of DNA involved in producing a polypeptide chain; it includes regions preceding and following the coding region (leader and trailer) as well as intervening sequences (introns) between individual coding segments (exons).

A coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

A "recombinant" protein or polypeptide refer to proteins or polypeptides produced by recombinant DNA techniques; i.e., produced from cells transformed by an exogenous DNA construct encoding the desired polypeptide (e.g. a Very long chain fatty acid coA-synthetase polypeptide of the present invention). "Synthetic" polypeptides are those prepared by chemical synthesis.

As used in connection with the present invention the term "polypeptide" or "protein" refers to a polymer in which the monomers are amino acid residues which are joined together through amide bonds. When the amino acids are alpha-amino acids, either the L-optical isomer or the D-optical isomer can be used, the L-isomers being preferred. The term "polypeptide" as used herein is intended to encompass any amino acid sequence and include modified sequences such as glycoproteins. The term "polypeptide" is specifically intended to cover naturally occurring proteins, as well as those which are recombinantly or synthetically synthesized, which occur in at least two different conformations wherein both conformations have the same or substantially the same amino acid sequence but have different three dimensional structures. "Fragments" are a portion of a naturally occurring protein. Fragments can have the same or substantially the same amino acid sequence as the naturally occurring protein. "Substantially the same" means that an amino acid sequence is largely, but not entirely, the same, but retains a functional activity of the sequence to which it is related. In general, two amino acid sequences are "substantially the same" or "substantially homologous" if they are at least 70% identical. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation, for example of possible modifications. The modified peptides can be chemically synthesized, or the isolated gene can be site-directed mutagenized, or a synthetic gene can be synthesized and expressed in bacteria, yeast, baculovirus, tissue culture and so on.

A DNA "coding sequence of" or a "nucleotide sequence encoding" a particular protein, is a DNA sequence which is transcribed and translated into an protein when placed under the control of appropriate regulatory sequences.

VLCFA coA-Synthetase Nucleic Acid, Polypeptides and Method of Expression

In one embodiment, the invention provides an isolated polynucleotide sequence encoding a VLCFA coA-syn polypeptide. An exemplary VLCFA coA-syn polypeptide of the invention has an amino acid sequence as set forth in SEQ ID NO:2. Polynucleotide sequences of the invention include DNA, cDNA and RNA sequences which encode VLCFA coA-syn. It is understood that all polynucleotides encoding all or a portion of VLCFA coA-syn are also included herein, so long as they encode a polypeptide with VLCFA coA-syn activity (e.g., increased life span or resistance to stress). Such polynucleotides include naturally occurring, synthetic, and intentionally manipulated polynucleotides. For example, VLCFA coA-syn polynucleotide may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention so long as the amino acid sequence of VLCFA coA-syn polypeptide encoded by the nucleotide sequence is functionally unchanged. Also included are nucleotide sequences which encode VLCFA coA-syn polypeptide, such as SEQ ID NO:1. In addition, the invention also includes a polynucleotide encoding a polypeptide having the biological activity of an amino acid sequence of SEQ ID NO:2 and having at least one epitope for an antibody immunoreactive with VLCFA coA-syn polypeptide. However, it is recognized that portions of either SEQ ID NO:1 or 2 may be excluded to identify fragments of the polynucleotide sequence or polypeptide sequence. For example, fragments of SEQ ID NO:1 or 2 are encompassed by the current invention, so long as they retain some biological activity related to VLCFA coA-syn. A biological activity related to VLCFA coA-syn includes for example, antigenicity or the ability to regulate β-oxidation of fatty acids.

The polynucleotides of this invention were originally recovered from *Drosophila melanogaster*. Thus, the present invention provides means for isolating the nucleic acid molecules from other organisms, including humans, encoding the polypeptides of the present invention. For example, one may probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated by one skilled in the art that probes can be designed based on the degeneracy of the genetic code to the sequences set forth in SEQ ID NO:2.

The invention includes polypeptides having substantially the same sequence as the amino acid sequence set forth in SEQ ID NO:2 or functional fragments thereof, or amino acid sequences that are substantially identical or the same as SEQ ID NO:2.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

Methods of alignment of sequence for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol 48:443 (1970), by the search for similarity method of person & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is BLAST and BLAST 2.0 algorithms, which are described in Altschul et al., Nuc. Acids Res. 25:3389–3402 (1977) and Altschul et al., J. Mol. Biol. 215:403–410 (1990), respectively. Software for performing BLAST analyses is publicly available through the National Center for Biotechnology Information on the world wide web at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) or 11, an expectation (E) or 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873 (1993)). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

A "substantially pure polypeptide" is typically pure when it is at least 60%, by weight, free from the proteins and naturally-occurring organic molecules with which it is naturally associated. Preferably, the preparation is at least 75%, more preferably at least 90%, and most preferably at least 99%, by weight, VLCFA coA-syn polypeptide. A substantially pure VLCFA coA-syn polypeptide may be obtained, for example, by extraction from a natural source (e.g., an insect cell); by expression of a recombinant nucleic acid encoding an VLCFA coA-syn polypeptide; or by chemically synthesizing the protein. Purity can be measured by any appropriate method, e.g., by column chromatography, polyacrylamide gel electrophoresis, or by HPLC analysis.

VLCFA coA-syn polypeptides of the present invention include peptides, or full length protein, that contains substitutions, deletions, or insertions into the protein backbone, that would still leave an approximately 50%–70% homology to the original protein over the corresponding portion. A yet greater degree of departure from homology is allowed if like-amino acids, i.e. conservative amino acid substitutions, do not count as a change in the sequence.

In addition to polypeptides of the invention, specifically disclosed herein is a DNA sequence for VLCFA coA-syn represented by SEQ ID NO:1. DNA sequences of the invention can be obtained by several methods. For example, the DNA can be isolated using hybridization or-computer-based techniques which are well known in the art. These include, but are not limited to: 1) hybridization of genomic libraries with probes to detect homologous nucleotide sequences; 2) antibody screening of expression libraries to detect cloned DNA fragments with shared structural features; 3) polymerase chain reaction (PCR) on genomic DNA using primers capable of annealing to the DNA sequence of interest; and 4) computer searches of sequence databases for similar sequences.

The polynucleotide encoding VLCFA coA-syn includes the nucleotide sequence in FIG. 3 (SEQ ID NO:1), as well as nucleic acid sequences complementary to that sequence. When the sequence is RNA, the deoxyribonucleotides A, G, C, and T of SEQ ID NO:1 are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes the protein of FIG. 3 (e.g., SEQ ID NO: 2). "Selective hybridization" as used herein refers to hybridization under moderately stringent or highly stringent physiological conditions (See, for example, the techniques described in Maniatis et al., 1989 *Molecular Cloning A Laboratory Manual*, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperatureh (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Oligonucleotides encompassed by the present invention are also useful as primers for nucleic acid amplification reactions. In general, the primers used according to the method of the invention embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15–22 or more nucleotides, although it may contain fewer nucleotides as long as the primer is of sufficient specificity to allow essentially only the amplification of the specifically desired target nucleotide sequence (i.e., the primer is substantially complementary).

Amplified products may be detected by Southern blot analysis, without using radioactive probes. In such a process, for example, a small sample of DNA containing a very low level of VLCFA coA-syn nucleotide sequence is amplified and analyzed via a Southern blotting technique known to those of skill in the art. The use of non-radioactive probes or labels is facilitated by the high level of the amplified signal.

VLCFA coA-syn polynucleotide of the invention is derived from an insect (e.g., Drosophila). Screening procedures which rely on nucleic acid hybridization make it possible to isolate any gene sequence from any organism, provided the appropriate probe is available. For example, it is envisioned that such probes can be used to identify other homologs of the VLCFA coA-syn family of factors in insects or, alternatively, in other organisms such as mammals, e.g., humans. In accomplishing this, oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of DNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

When the entire sequence of amino acid residues of the desired polypeptide is not known, the direct synthesis of DNA sequences is not possible and the method of choice is use of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned.

DNA sequences encoding VLCFA coA-syn can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

In the present invention, the VLCFA coA-syn polynucleotide sequences may be inserted into a recombinant expression vector. The term "recombinant expression vector" refers to a plasmid, virus or other vehicle known in the art that has been manipulated by insertion or incorporation of the VLCFA coA-syn genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells.

Vectors suitable for use in the present invention include those described above.

Polynucleotide sequences encoding VLCFA coA-syn can be expressed in either prokaryotes or eukaryotes. Hosts can include microbial, yeast, insect and mammalian organisms. Such vectors are used to incorporate DNA sequences of the invention.

Methods which are well known to those skilled in the art can be used to construct expression vectors containing the VLCFA coA-syn coding sequence and appropriate transcriptional/translational control signals. These methods include in vitro recombinant DNA techniques, synthetic techniques, and in vivo recombination/genetic techniques. (See, for example, the techniques described in Maniatis et al., 1989, *Molecular Cloning A Laboratory Manual*, Cold Spring Harbor Laboratory, N.Y.)

The genetic construct can be designed to provide additional benefits, such as, for example addition of C-terminal or N-terminal amino acid residues that would facilitate purification by trapping on columns or by use of antibodies. All those methodologies are cumulative. For example, a synthetic gene can later be mutagenized. The choice as to the method of producing a particular construct can easily be made by one skilled in the art based on practical considerations: size of the desired peptide, availability and cost of starting materials, etc. All the technologies involved are well established and well known in the art. See, for example, Ausubel et al., *Current Protocols in Molecular Biology*, Volumes 1 and 2 (1987), with supplements, and Maniatis et al., *Molecular Cloning, a Laboratory Manual*, Cold Spring Harbor Laboratory (1989). Yet other technical references are known and easily accessible to one skilled in the art.

Antibodies That Bind to VLCFA coa-syn

In another embodiment, the present invention provides antibodies that bind to VLCFA coA-syn. Such antibodies are useful for research and diagnostic tools in the study of neurodegeneration, ALD and VLCFA coA-synthetase associated pathologies in general. Such antibodies may be administered alone or contained in a pharmaceutical composition comprising antibodies against VLCFA coA-syn and other reagents effective as modulators neurodegeneration, β-oxidation of fatty acids both in vitro and in vivo.

The term "epitope", as used herein, refers to an antigenic determinant on an antigen, such as a VLCFA coA-syn polypeptide, to which the paratope of an antibody, such as an VLCFA coA-syn-specific antibody, binds. Antigenic determinants usually consist of chemically active surface groupings of molecules, such as amino acids or sugar side chains, and can have specific three-dimensional structural characteristics, as well as specific charge characteristics.

Antibodies which bind to the VLCFA coA-syn polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

An antibody suitable for binding to VLCFA coA-syn is specific for at least one portion of a region of the VLCFA coA-syn polypeptide, as shown in FIG. 3 (SEQ ID NO:2). For example, one of skill in the art can use the peptides to generate appropriate antibodies of the invention. Antibodies of the invention include polyclonal antibodies, monoclonal antibodies, and fragments of polyclonal and monoclonal antibodies.

The preparation of polyclonal antibodies is well-known to those skilled in the art. See, for example, Green et al., *Production of Polyclonal Antisera*, in *Immunochemical Protocols* (Manson, ed.), pages 1–5 (Humana Press 1992); Coligan et al., *Production of Polyclonal Antisera in Rabbits, Rats, Mice and Hamsters*, in *Current Protocols in Immunology*, section 2.4.1 (1992), which are hereby incorporated by reference.

The preparation of monoclonal antibodies likewise is conventional. See, for example, Kohler & Milstein, *Nature*, 256:495 (1975); Coligan et al., sections 2.5.1–2.6.7; and Harlow et al., *Antibodies: A Laboratory Manual*, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., *Purification of Immunoglobulin G (IgG)*, in *Methods in Molecular Biology*, Vol. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., *Int. J. Cancer*, 46:310 (1990), which are hereby incorporated by reference.

Alternatively, an; anti-VLCFA coA-syn antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA*, 86:3833 (1989), which is hereby incorporated in its entirety by reference. Techniques for producing humanized monoclonal antibodies are described, for example, by Jones et al., *Nature*, 321: 522 (1986); Riechmann et al., *Nature*, 332: 323 (1988); Verhoeyen et al., *Science*, 239:1534 (1988); Carter et al., *Proc. Nat'l Acad. Sci. USA*, 89:4285 (1992); Sandhu, *Crit. Rev. Biotech.*, 12:437 (1992); and Singer et al., *J. Immunol.*, 150:2844 (1993), which are hereby incorporated by reference.

Antibodies of the invention also may be derived from human antibody fragments isolated from a combinatorial immunoglobulin library. See, for example, Barbas et al., *Methods: A Companion to Methods in Enzymology, Vol. 2*, page 119 (1991); Winter et al., *Ann. Rev. Immunol.* 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.*, 7:13 (1994); Lonberg et al., *Nature*, 368:856 (1994); and Taylor et al., *Int. Immunol.*, 6:579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$ This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoff et al., *Arch. Biochem. Biophys,*. 89:230 (1960); Porter, *Biochem. J.*, 73:119 (1959); Edelman et al., *Methods in Enzymology*, Vol. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA*, 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology, Vol. 2*, page 97 (1991); Bird et al., *Science*, 242:423 (1988); Ladner et al., U.S. Pat. No. 4,946,778; Pack et al., *Bio/Technology*, 11:1271 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: *A Companion to Methods in Enzymology, Vol. 2*, page 106 (1991).

Modulation of Neurodegeneration or Survival

In one embodiment, the invention provides a method for modulating (e.g., reducing) neurodegeneration in a cell or a subject by administering to the cell or subject a therapeutically effective amount of a composition which contains an VLCFA coA-syn polypeptide, or biologically functional fragment thereof or an agent (e.g, an antibody, ribozyme, antisense molecule, or double-stranded interferring RNA molecules). The term "biologically functional fragment" encompasses any segment of a VLCFA coA-syn polypeptide that retains the ability to modulate (e.g., increase or decrease) β-oxidation of VLCFA or which retains acyl-coA sythetase activity.

As used herein, a "therapeutically effective amount" of a composition containing VLCFA coA-syn or an VLCFA coA-syn-modulating agent is defined as that amount that is effective in modulating β-oxidation of VLCFAs.

In another embodiment, the present invention provides a method for modulating VLCFA coA-syn gene expression and well as methods for screening for agents which modulate VLCFA coA-syn gene expression. A cell or subject is contacted with an agent suspected or known to have VLCFA coA-syn gene expression modulating activity. The change in VLCFA coA-syn gene expression is then measured as compared to a control or standard sample. The control or standard sample can be the baseline expression of the cell or subject prior to contact with the agent. An agent which modulates VLCFA coA-syn gene expression may be a polynucleotide for example. The polynucleotide may be an antisense, a triplex agent, a ribozyme, or a double-stranded interferring RNA. For example, an antisense may be directed to the structural gene region or to the promoter region of VLCFA coA-syn. The agent may be an agonist, antagonist, peptide, peptidomimetic, antibody, or chemical. Double-stranded interferring RNA molecules are especially useful in the present invention. Such molecules act to inhibit expression of a target gene. For example, double-stranded RNA molecules can be injected into a target cell or organism to inhibit expression of a gene and the resultant gene products activity. It has been found that such double-stranded RNA molecules are more effective at inhibiting expression than either RNA strand alone. (Fire et al., *Nature*, 1998, 19:391(6669):806–11).

When a disorder is associated with abnormal expression of VLCFA coA-syn, a therapeutic approach which directly interferes with the translation of VLCFA coA-syn messages into protein is possible. Alternatively, similar methodology may be used to study VLCFA coA-syn gene activity. For example, antisense nucleic acid, double-stranded interferring RNA or ribozymes could be used to bind to the VLCFA coA-syn mRNA or to cleave it. Antisense RNA or DNA molecules bind specifically with a targeted gene's RNA message, interrupting the expression of that gene's protein product. The antisense binds to the messenger RNA forming a double stranded molecule which cannot be translated by the cell. Antisense oligonucleotides of about 15–25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. These and other uses of antisense methods to inhibit the in vitro translation of genes are well known in the art (Marcus-Sakura, *Anal. Biochem.*, 172:289, 1988).

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target VLCFA coA-syn-producing cell. The use of antisense methods to inhibit the in vitro translation of genes is well known in the art (Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1:227, 1991; Helene, *Anticancer Drug Design*, 6:569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

These and other uses of antisense methods to inhibit the in vivo translation of genes are well known in the art (e.g., De Mesmaeker, et al., *Curr. Opin. Struct. Biol.*, 5:343, 1995; Gewirtz, A. M., et al., *Proc. Natl. Acad. Sci. U.S.A.*, 93:3161, 1996b; Stein, C. A., *Chem. and Biol.* 3:319, 1996).

Delivery of antisense, triplex agents, ribozymes, competitive inhibitors, double-stranded interferring RNA and the like can be achieved using a recombinant expression vector such as a chimeric virus or a colloidal dispersion system or by injection. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

The agents useful in the method of the invention can be administered, for in vivo application, parenterally by injection or by gradual perfusion over time. Administration may be intravenously, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

Pharmaceutical Compositions

It is envisioned that the methods of the present invention can be used to treat pathologies associated with neurodegeneration. Therefore, the present invention encompasses methods for ameliorating a disorder associated with VLCFA coA-syn, including treating a subject having the disorder, at the site of the disorder, with a VLCFA coA-syn reactive agent. Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure for an infection or disease and/or adverse effect attributable to the infection or disease. "Treating" as used herein covers any treatment of, or prevention of, an infection or disease in an invertebrate, a vertebrate, a mammal, particularly a human, and includes:

(a) preventing the disease from occurring in a subject that may be predisposed to the disease, but has not yet been diagnosed as having it;

(b) inhibiting the disease, i.e., arresting its development; or (c) relieving or ameliorating the disease, i.e., cause regression of the disease.

However, it should be recognized that the compositions and methods described herein, can be used to bring about a desired result (e.g., an increase in life span, increase β-oxidation of VLCFAs and a decrease in VLCFAs) in the absence of a disease or disorder.

Thus, the invention includes various pharmaceutical compositions useful for ameliorating symptoms attributable to a VLCFA coA-syn-associated disorder. The pharmaceutical compositions according to the invention are prepared by bringing an antibody against VLCFA coA-syn, a polypeptide or peptide derivative of VLCFA coA-syn, a VLCFA coA-syn mimetic, a drug, chemical or combination of chemicals (e.g., a combination of oils) or a VLCFA coA-syn-binding agent according to the present invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences*, 15th ed. Easton: Mack Publishing Co., 1405–1412, 1461–1487 (1975) and *The National Formulary XIV.*, 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's *The Pharmacological Basis for Therapeutics* (7th ed.).

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, *Science*, 249: 1527, (1990); Gilman et al. (eds.) (1990), each of which is herein incorporated by reference.

In one embodiment, the invention provides a pharmaceutical composition useful for administering a VLCFA coA-syn polypeptide, or nucleic acid encoding a VLCFA coA-syn polypeptide, to a subject in need of such treatment. "Administering" the pharmaceutical composition of the present invention may be accomplished by any means known to the skilled artisan. Preferably a "subject" refers to a mammal, most preferably a human, but may be any organism.

The VLCFA coA-syn protein or antibody can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

Screening Assay for Compounds That Affect VLCFA coA-syns

In another embodiment, the invention provides a method for identifying a compound which modulates VLCFA coA-syn expression or activity including incubating components comprising the compound and a VLCFA coA-syn polypeptide, or a recombinant cell expressing a VLCFA coA-syn polypeptide, under conditions sufficient to allow the components to interact and determining the affect of the compound on the expression or activity of the gene or polypeptide, respectively. The term "affect", as used herein, encompasses any means by which VLCFA coA-syn gene expression or protein activity can be modulated. Such compounds can include, for example, polypeptides, peptidomimetics, chemical compounds and biologic agents as described below.

Incubating includes conditions which allow contact between the test compound and VLCFA coA-syn, a cell expressing VLCFA coA-syn or nucleic acid encoding VLCFA coA-syn. Contacting includes in solution and in solid phase. The test ligand(s)/compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Thus, the method of the invention includes combinatorial chemistry methods for identifying chemical compounds that bind to VLCFA coA-syn or affect VLCFA coA-syn expression or activity. By providing for the production of large amounts of a VLCFA coA-syn, one can identify ligands or substrates that bind to, modulate, affect the expression of, or mimic the action of a VLCFA coA-syn. For example, a polypeptide may have biological activity associated with the wild-type protein, or may have a loss of function mutation due to a point mutation in the coding sequence, substitution, insertion, deletion and scanning mutations.

Areas of investigation are the development of therapeutic treatments. The screening identifies agents that provide modulation of VLCFA coA-syn function in targeted organisms. Of particular interest are screening assays for agents that have a low toxicity for humans. A wide variety of assays may be used for this purpose, including labeled in vitro protein-protein binding assays, protein-DNA binding assays, electrophoretic mobility shift assays, immunoassays for protein binding, and the like. The purified protein may also be used for determination of three-dimensional crystal structure, which can be used for modeling intermolecular interactions, for example.

The term "agent" as used herein describes any molecule, e.g. protein or pharmaceutical, with the capability of altering or mimicking the physiological function or expression of a VLCFA coA-syn. Generally, a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification and amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors and anti-microbial agents may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

In addition, cells or organisms which have a mutation in a VLCFA-coA synthetase may be use as models to screen for agents which modulate disorders associated with the mutation. For example, the inventors have identified that organisms (e.g., Drosophila) which lack VLCFA coA-synthetase demonstrate a phenotype similar to ALD resulting in neurodegeneration and a shortened life-span. Accordingly, administration of agents to organism having such a mutation, or cells derived or recombinantly modified to have a reduced VLCFA coA-synthetase activity may be used to determine the effect of the drug or agent on neurodegeneration.

Detection of VLCFA coA-syn in Vivo and in Vitro

In a further embodiment, the invention provides a method of detecting VLCFA coA-syn or a VLCFA coA-syn-associated disorder in a subject including contacting a cell component containing VLCFA coA-syn with a reagent which binds to the cell component. The cell component can be nucleic acid, such as DNA or RNA, or it can be protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other labels suitable for binding to an antibody or nucleic acid probe, or will be able to ascertain such, using routine experimentation.

For purposes of the invention, an antibody or nucleic acid probe specific for VLCFA coA-syn may be used to detect the presence of VLCFA coA-syn polypeptide (using antibody) or polynucleotide (using nucleic acid probe) in biological fluids or tissues. Any specimen containing a detectable amount of VLCFA coA-syn antigen or polynucleotide can be used. In addition, antibodies and polynucleotides designed to recognize mutations in a VLCFA coA-synthetase polypeptide or polynucleotide may be used. For example, specimens of this invention include blood, urine, cerebrospinal fluid, synovial fluid or any tissue.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, VLCFA coA-syn polypeptide can be used to detect antibodies to VLCFA coA-syn polypeptide in a specimen. The VLCFA coA-syn of the invention is particularly suited for use in immunoassays in which it can be utilized in liquid phase or bound to a solid phase carrier. In addition, VLCFA coA-syn used in these assays can be detectably labeled in various ways.

Examples of immunoassays which can utilize the VLCFA coA-syn of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to the VLCFA coA-syn of the invention can be done utilizing immunoassays which run in either the forward, reverse, or simultaneous modes, including immunohistochemical assays on physiological samples. The concentration of VLCFA coA-syn which is used will vary depending on the type of immunoassay and nature of the detectable label which is used. However, regardless of the type of immunoassay which is used, the concentration of VLCFA coA-syn utilized can be readily determined by one of ordinary skill in the art using routine experimentation.

The VLCFA coA-syn of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding VLCFA coA-syn or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to VLCFA coA-syn of the invention may be present in various biological fluids and tissues. Any sample containing a detectable amount of antibodies to VLCFA coA-syn can be used. Typically, a sample is a liquid such as urine, saliva, cerebrospinal fluid, blood, serum and the like, or a solid or semi-solid such as tissue, feces and the like.

The monoclonal antibodies of the invention, directed toward VLCFA coA-syn, are also useful for the in vivo detection of antigen. The detectably labeled monoclonal antibody is given in a dose which is diagnostically effective. The term "diagnostically effective" means that the amount of detectably labeled monoclonal antibody is administered in sufficient quantity to enable detection of VLCFA coA-syn antigen for which the monoclonal antibodies are specific.

The concentration of detectably labeled monoclonal antibody which is administered should be sufficient such that the binding to those cells, body fluid, or tissue having VLCFA coA-syn is detectable compared to the background. Further, it is desirable that the detectably labeled monoclonal antibody be rapidly cleared from the circulatory system in order to give the best target-to-background signal ratio.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of a VLCFA coA-syn-associated disorder. Thus, by measuring the increase or decrease of VLCFA coA-syn polypeptide present in various body fluids or tissues, it would be possible to determine whether a particular therapeutic regiment aimed at ameliorating the disorder is effective.

In another embodiment, nucleic acid probes can be used to identify VLCFA coA-syn nucleic acid from a specimen obtained from a subject. Examples of specimens from which nucleic acid sequence encoding VLCFA coA-syn can be derived include insect, human, swine, porcine, feline, canine, equine, murine, cervine, caprine, lupine, leporidine and bovine species.

Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9:879, 1981).

In an embodiment of the invention, purified nucleic acid fragments containing intervening sequences or oligonucleotide sequences of 10–50 base pairs are radioactively labeled. The labeled preparations are used to probe nucleic acid from a specimen by the Southern hybridization technique. Nucleotide fragments from a specimen, before or after amplification, are separated into fragments of different molecular masses by gel electrophoresis and transferred to filters that bind nucleic acid. After exposure to the labeled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72–81). Alternatively, nucleic acid from the specimen can be bound directly to filters to which the radioactive probe selectively attaches by binding nucleic acids having the sequence of interest. Specific sequences and the degree of binding is quantitated by directly counting the radioactive emissions.

Where the target nucleic acid is not amplified, detection using an appropriate hybridization probe may be performed directly on the separated nucleic acid. In those instances where the target nucleic acid is amplified, detection with the appropriate hybridization probe would be performed after amplification.

For the most part, the probe will be detectably labeled with an atom or inorganic radical, most commonly using radionuclides, but also heavy metals can be used. Conveniently, a radioactive label may be employed. Radioactive labels include $^{32}P$, $^{125}I$, $^{3}H$, $^{14}C$, $^{111}In$, $^{99m}Tc$, or the like. Any radioactive label may be employed which provides for an adequate signal and has sufficient half-life. Other labels include ligands, which can serve as a specific binding pair member for a labeled ligand, and the like. A wide variety of labels routinely employed in immunoassays can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}P$-dNTP or terminal phosphate hydrolysis with alkaline phosphatase followed by labeling with radioactive $^{32}P$ employing $^{32}P$-NTP and T4 polynucleotide kinase. Alternatively, nucleotides can be synthesized where one or more of the elements present are replaced with a radioactive isotope, e.g., hydrogen with tritium. If desired, complementary labeled strands can be used as probes to enhance the concentration of hybridized label.

Where other radionucleotide labels are involved, various linking groups can be employed. A terminal hydroxyl can be esterified, with inorganic acids, e.g., $^{32}P$ phosphate, or $^{14}C$ organic acids, or else esterified to provide linking groups to the label. Alternatively, intermediate bases may be substituted with activatable linking groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2, 3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports that can be used in the method of the invention.

The nucleic acid from a specimen can be cloned and then spotted or spread onto a filter to provide a plurality of individual portions (plaques). The filter is an inert porous solid support, e.g., nitrocellulose. Any cells (or phage) present in the specimen are treated to liberate their nucleic acid. The lysing and denaturation of nucleic acid, as well as the subsequent washings, can be achieved with an appropriate solution for a sufficient time to lyse the cells and denature the nucleic acid. For lysing, chemical lysing will conveniently be employed, as described previously for the lysis buffer. Other denaturation agents include elevated temperatures, organic reagents, e.g., alcohols, amides, amines, ureas, phenols and sulfoxides or certain inorganic ions, e.g., thiocyanate and perchlorate.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. Under this procedure, the nucleic acid is fixed in position and can be assayed with the probe when convenient.

Pre-hybridization may be accomplished by incubating the filter with the hybridization solution without the probe at a mildly elevated temperature for a sufficient time to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300–500 kDa), polyvinylpyrrolidone, (about 250–500 kDa) and serum albumin. Also included in the hybridization solution will generally be from about 0.5 to 5 mg/ml of sonicated denatured DNA, e.g., calf thymus of salmon sperm; and optionally from about 0.5 to 2% wt/vol glycine. Other additives may also be included, such as dextran sulfate of from about 100 to 1,000 kDa and in an amount of from about 8 to 15 weight percent of the hybridization solution.

The particular hybridization technique is not essential to the invention. Other hybridization techniques are described by Gall and Pardue, (*Proc. Natl. Acad. Sci.* 63:378, 1969); and John, et al., (*Nature*, 223:582, 1969). As improvements are made in hybridization techniques they can readily be applied in the method of the invention.

The amount of labeled probe present in the hybridization solution will vary widely, depending upon the nature of the label, the amount of the labeled probe that can reasonably bind to the filter, and the stringency of the hybridization. Generally, substantial excess over stoichiometric concentrations of the probe will be employed to enhance the rate of binding of the probe to the fixed target nucleic acid.

In nucleic acid hybridization reactions, the conditions used to achieve a particular level of stringency will vary, depending on the nature of the nucleic acids being hybridized. For example, the length, degree of complementarity, nucleotide sequence compound (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The label may also comprise a fluorescent moiety that can then be probed with a specific fluorescent antibody. Horseradish peroxidase enzyme can be conjugated to the antibody to catalyze a chemiluminescent reaction. Production of light can then be seen on rapid exposure to film.

Transgenic Organisms

The present invention also contemplates transgenic non-human organisms, including invertebrates, vertebrates and mammals. For purposes of the subject invention, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene integrated into the chromosomes of somatic cells.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene. chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a published procedure by Love et al., (Biotechnology, Jan. 12, 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention include, for example, bovine, porcine, ovine and avian animals (e.g., cow, pig, sheep, chicken, turkey). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. The use of zygotes as a target for gene transfer has a major advantage in that in most cases the injected DNA will be incorporated into the host gene before the first cleavage (Brinster et al., *Proc. Natl. Acad. Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci. USA* 82:6927–6931, 1985; Van der Putten, et al., *Proc. Natl. Acad. Sci USA* 82:6148–6152, 1985). Transfection is easily and efficiently obtained by culturing the blastomeres on a monolayer of virus-producing cells (Van der Putten, supra; Stewart, et al., *EMBO J.* 6:383–388, 1987). Alternatively, infection can be performed at a later stage. Virus or virus-producing cells can be injected into the blastocoele (D. Jahner et al., *Nature* 298:623–628, 1982).

Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., *Proc. Natl. Acad. Sci USA* 83: 9065–9069, 1986; and Robertson et.al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode VLCFA coA-syn, and include VLCFA coA-syn-sense, antisense, dominant negative encoding polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout (i.e., knockout of VLCFA coA-synthetase). The term "gene knockout" as used herein, refers to the targeted disruption of a gene in vivo with complete or partial loss of function that has been achieved by any transgenic technology familiar to those in the art (e.g., insertion of a P-element in Drosophila). In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

In one embodiment, the transgene comprises DNA antisense to the coding sequence for VLCFA coA-syn. In another embodiment, the transgene comprises DNA encoding an antibody which is able to bind to VLCFA coA-syn.

Where appropriate, DNA sequences that encode proteins having VLCFA coA-syn activity but differ in nucleic acid sequence due to the degeneracy of the genetic code may also be used herein, as may truncated forms, allelic variants and interspecies homologues.

The invention also includes animals having heterozygous mutations in VLCFA coA-syn or partial inhibition of VLCFA coA-syn function or expression. Partial loss of function leads to a decrease in $\beta$-oxidation of VLCFAs resulting in a phenotype characteristic of ALD (e.g., neurodegeneration and shortened lifespan). One of skill in the art would readily be able to determine if a particular mutation or if an antisense molecule was able to partially inhibit VLCFA coA-syn. For example, in vitro testing may be desirable initially by comparison with wild-type or untreated VLCFA coA-syn (e.g., comparison of northern blots to examine a decrease in expression).

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1) which are analyzed for transgene expression by Northern blot analysis of tissue samples. To be able to distinguish expression of like-species transgenes from expression of the animals endogenous VLCFA coA-syn gene(s), a marker gene fragment can be included in the construct in the 3' untranslated region of the transgene and the Northern probe designed to probe for the marker gene fragment. The serum levels of VLCFA coA-syn can also be measured in the transgenic animal to establish appropriate expression.

Expression of the VLCFA coA-syn transgenes, thereby decreasing the VLCFA coA-syn in the tissue and serum levels of the transgenic animals.

Transgenic organisms of the invention are highly useful in the production of organisms for study of neurodegeneration and in identifying agents or drugs with inhibit or modulate neurodegeneration (e.g., ALD).

It will be recognized that the method of crating a transgenic organism include methods of inserting a transgene into, for example, an embryo of an already created transgenic organism, the organism being transgenic for a different unrelated gene or gene product.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLES

Mutagenesis and screen. Drosophilia lines carrying P(lacZ, w+) were screened for mutations causing reduced lifespan at 29° C. Candidates showing reduced lifespan compared with the parent strain were examined after aging, but before death, to identify those with brain degeneration, bubblegum showed early death associated with degeneration.

Figure 1A:
FIGS. 1A–C is a horizontal histological section of the optic lobe of an adult male fly. (A) Young mutant fly (1 day old). (B) 15 day old mutant. La, Lamina; Re, Retina. Scale bar: 50 μm. (C) Survival curve of bubblegum males, compared with parental strain.
Figure 1B:
Figure 1C:
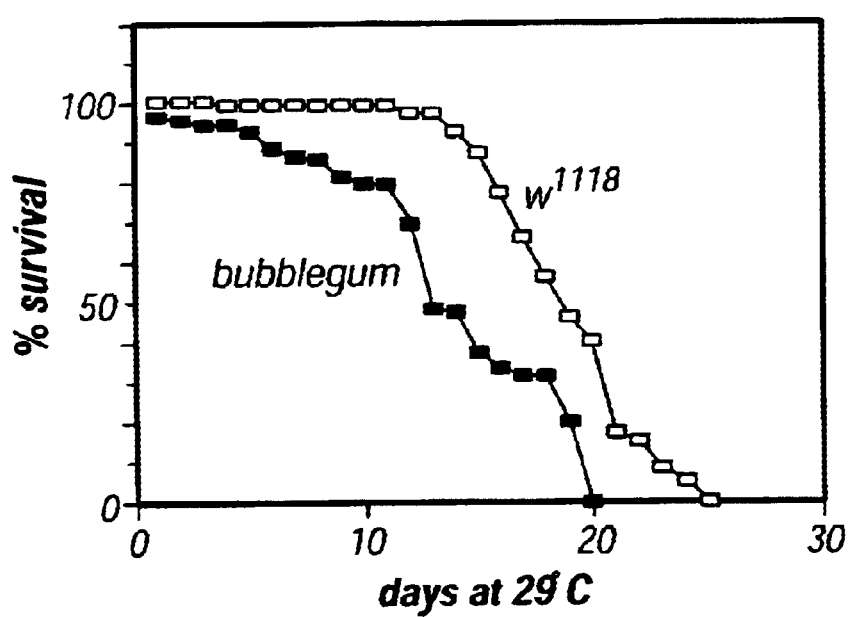
Figure 3B-1:
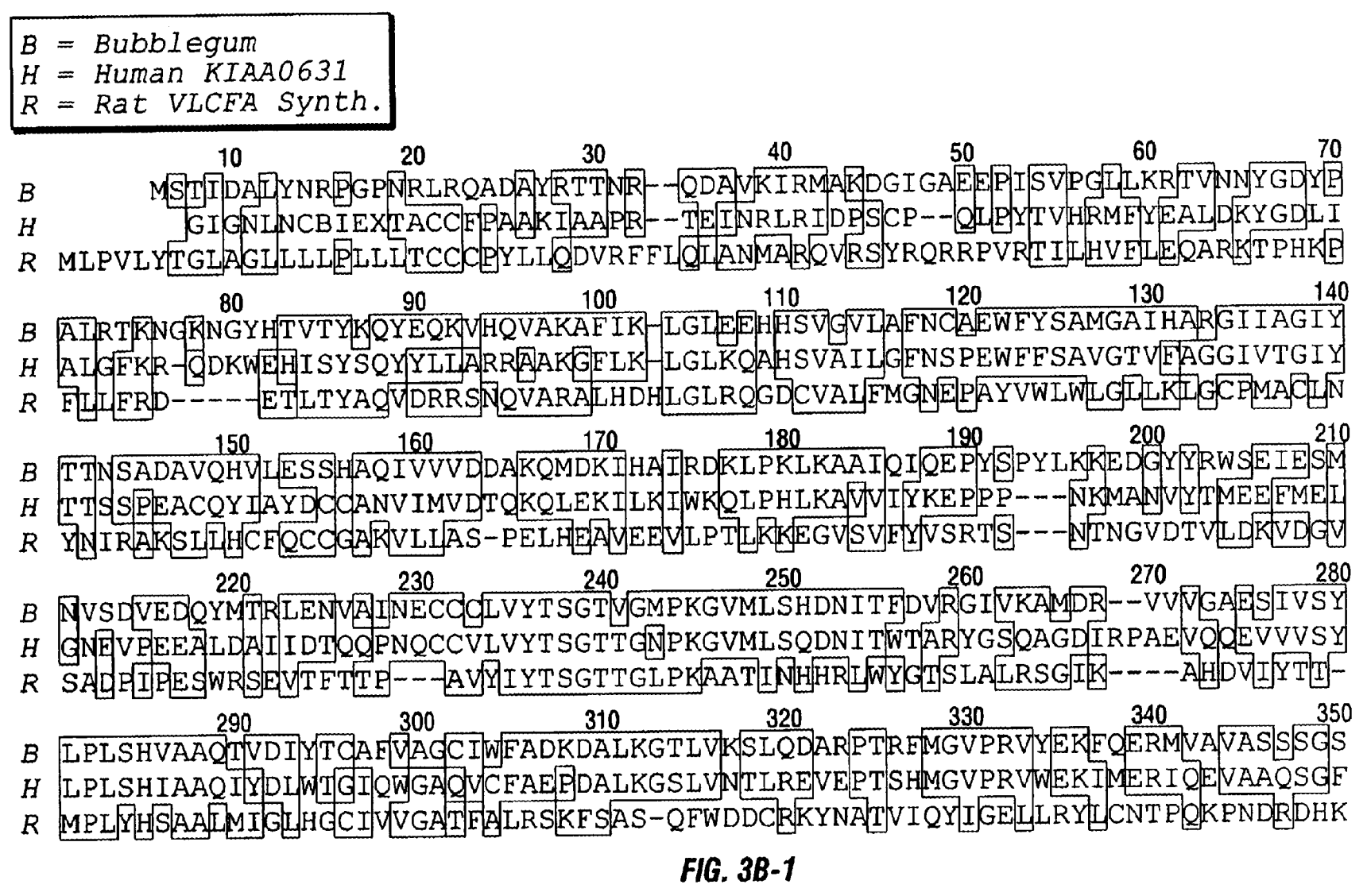

To identify the affected gene in bubblegum, genomic DNA adjacent to P-element insertion was isolated by plasmid rescue and sequenced. The genomic sequence of the region had been determined by the Berkeley genome project and a cDNA clone for the gene was commercially available. The P-element was found to be inserted into the region between the 5' UTR and the start codon of an open reading frame of 2502 bp predicting a protein of 649 amino acids (FIGS. 3A1, 3A2 and 3A3). A Blast protein data bank search indicated homology with very long chain fatty acid acyl CoA synthetase in the rat (FIGS. 3B1 and 3B2). The overall similarity between the two proteins is 53%. A human sequence closely similar to the rat was also identified (FIGS. 3B1 and 3B2).

Tissue preparation for microscopy. Fly heads were prepared by fixation in 1% paraformaldehyde+1% glutaraldehyde, postfixation in 1% osmium tetroxide, dehydration in an ethanol series, and embedding in Epon 812. For light microscopy, 1 m series were stained with 1% toludine blue 1% Borax. For electron microscopy, ultrathin sections (80 nm) were examined with a Philips 201 electron microscope at 60 kV.

Molecular cloning of the bubblegum gene. Genomic DNA sequences adjacent to the P-element insertion were identified via data from the Drosophila Berkeley genome project. The cDNA clone containing the bubblegum gene was purchased from Genome Systems. A single insertion of the P-element was confirmed by genomic Southern blots. Precise excision of the P-element from the mutant restored the normal phenotype.

Figure 4A:
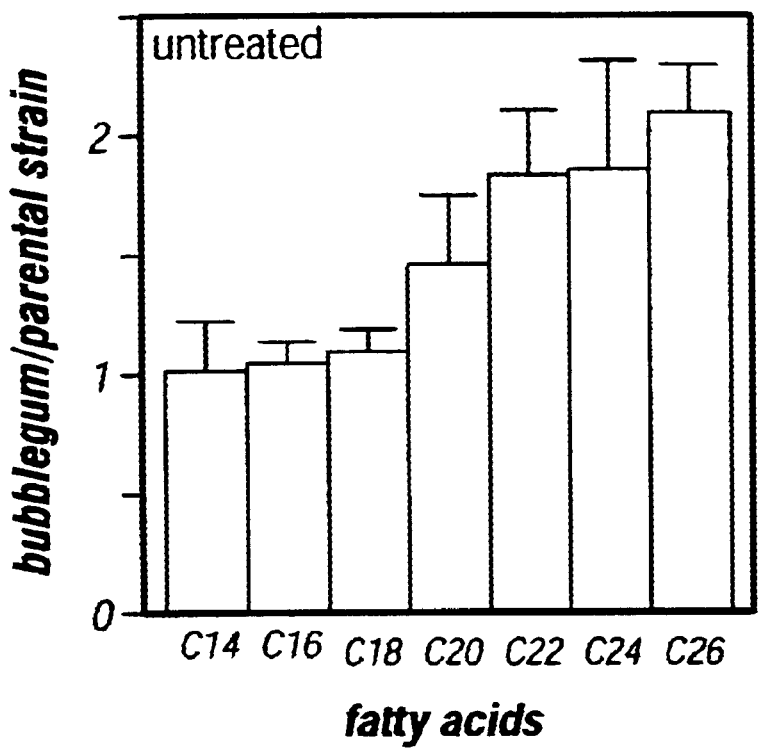
FIGS. 4A and 4B show the effect of dietary oil treatment on the spectrum of very long chain fatty acids in a bubblegum mutant fly. (A) Without oil treatment. (B) GTO-treated. Each fatty acid was measured as a percentage of the total. Bars represent ratios of bubblegum to the parental strain. Both being 15 days old.
Figure 4B:
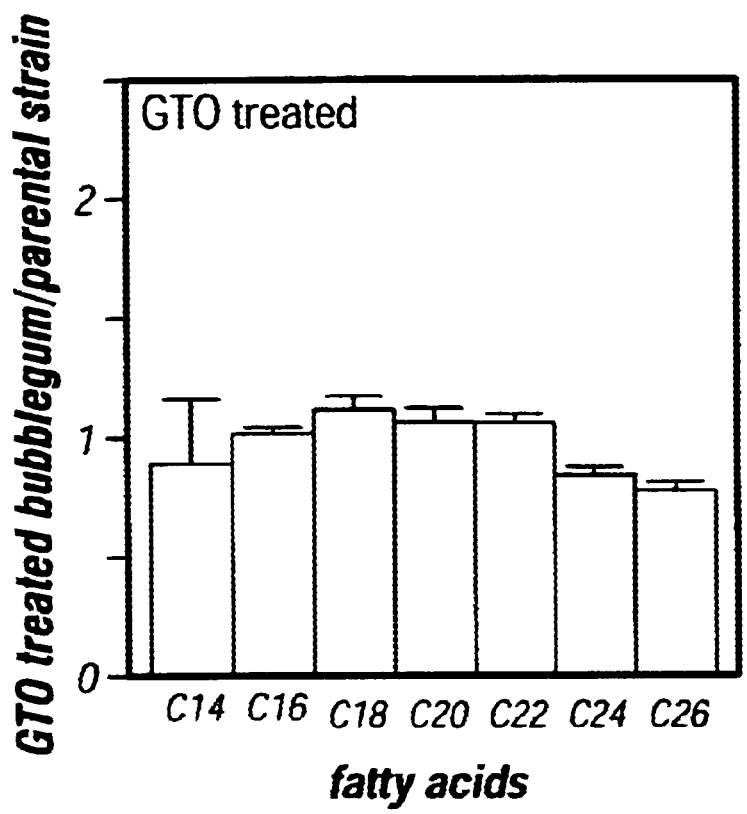

Assay of very long chain fatty acids by gas chromatography. To determine whether bubblegum has an accumulation of VLCFAs, fatty acid analysis by gas chromatography was performed on 15 day old flies, comparing homozygous mutant flies with those of the parent strain from which bubblegum was derived. Indeed, the mutant males showed increased levels of VLCFAs, including C22, C24, and C26 whereas those of chain length below C20 did not increase (FIG. 4).

Extracts of whole male or female flies were used for purification and methylation of fatty acids. Gas chromatography was performed with a HP-5MS column (30 m×0.25 mm, 0.25-$\mu$m film thickness) and mass spectrometry was used to analyze the fatty acid methyl esters. Identification and measurement of fatty acid concentrations were based on an oil reference standard (NHI-F) from Sigma Co. and the C15 added as an internal standard.

Figure 5A:
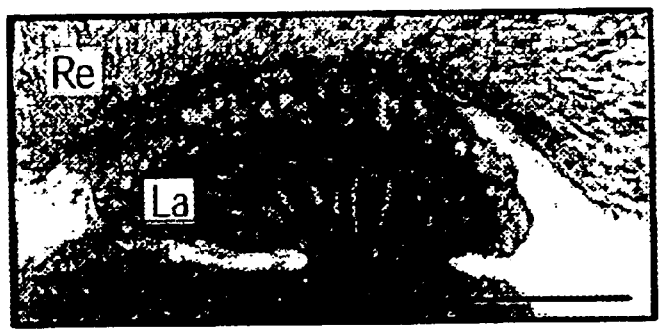
FIGS. 5A–C shows prevention of degeneration and the effect of glycerol trioleate treatment of bubblegum mutants. (A) bubblegum mutants fed with GTO for 15 days following emergence. (B) Fifteen day old adult bubblegum mutants that had been raised in medium containing GTO from the larval stage. Degeneration largely prevented. Scale bar: 50 µm. (C) Countercurrent phototaxis analysis of 5 day old bubblegum. Flies raised without GTO show poor performance. Flies pretreated with GTO from the larval stage showed greatly enhanced response to the light.
Figure 5B:

To determine whether similar dietary treatment can reduce the level of C26 and/or prevent the pathology seen in bubblegum, 2.5% of GTO oil was added to the normal corn meal-yeast-agar medium. When adult mutant flies were transferred to that medium, the onset of brain degeneration was reduced only slightly; the photoreceptor axons in the lamina still expanded (FIG. 5a). However, knowing that oil treatment in ALD was not able to prevent the progression of the disease once patients had shown neurological symptoms, we decided to treat mutant flies with the oil at pre-adult stages. First instar larvae were raised in the oil-containing medium until eclosion and the adult flies were then transferred into fresh medium, still containing the oil, changed every 3 days. Both light microscopy and electron microscopy of 15 day-old adult flies revealed that the degeneration in the oil-treated mutant flies had largely been prevented (FIG. 5b). In addition, the levels of VLCFAs were reduced to normal (FIG. 4b), and the lifespan recovered. The oil had no evident effects on flies with the normal gene.

Figure 5C:
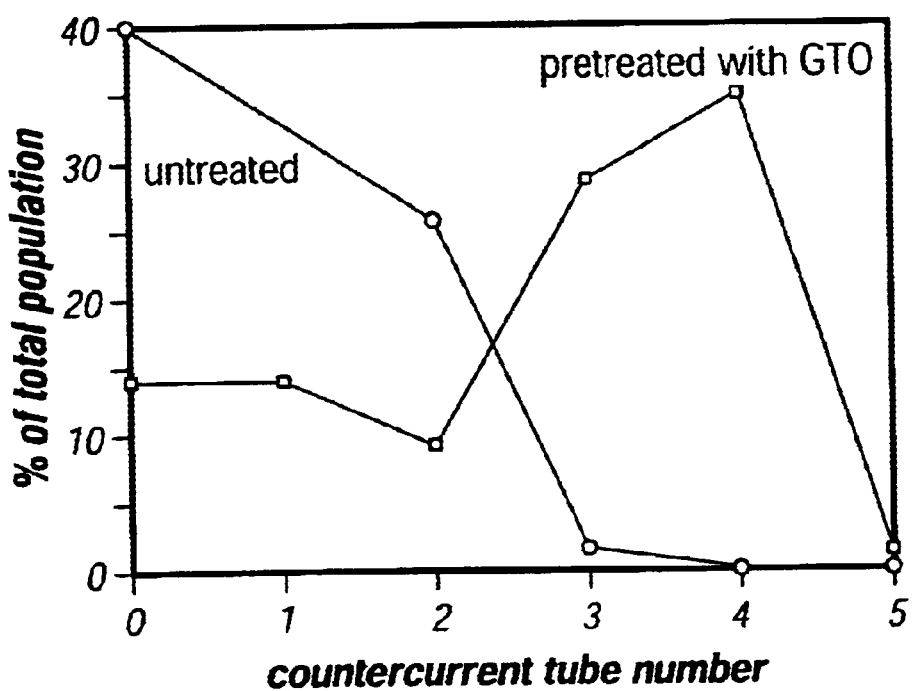
Figure 6:
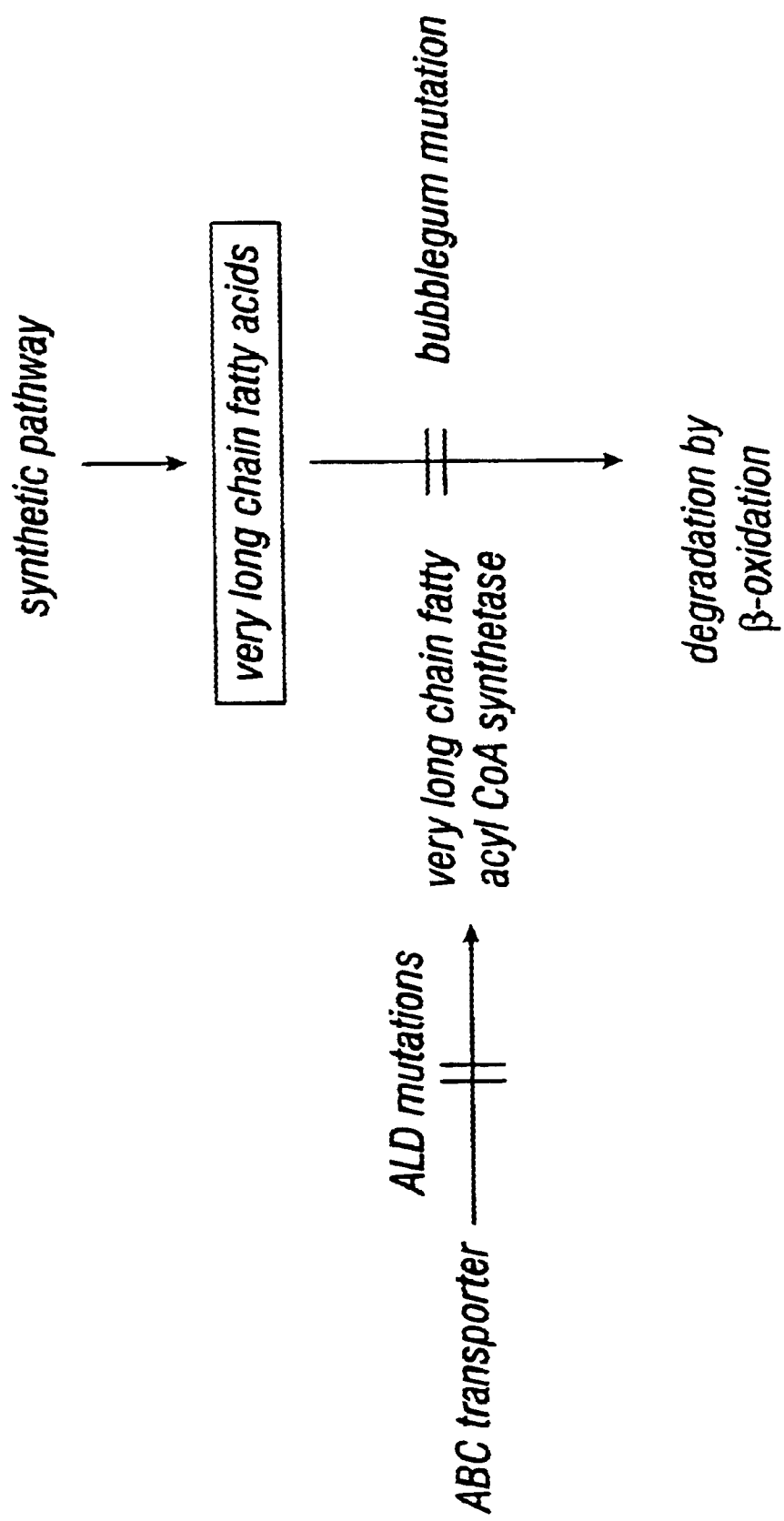
FIG. 6 shows a schematic of a pathway identifying the location and affect the bubblegum mutant has in the degradation of VLCFAs by β-oxidation. Normally, the synthetase activates VLCFAs for degradation. In ALD patients a genetic defect in an ABC transporter interferes with the function of the synthetase. As a consequence, there is an excess accumulation of VLCFAs. In the bubblegum mutant, a similar effect is due to a mutation in the synthetase itself.

Phototactic analysis. In ALD, visual loss is on of the clinical symptoms, and anatomical analysis has shown abnormalities of the optic nerve and degeneration of ganglion cell layer. Flies transformed with P-elements expressing eye pigment, as is the case for bubblegum, are phototactic. A countercurrent phototaxis test was used to examine the visual behavior of bubblegum. While mutant flies, raise in ordinary medium, showed little response, those raised with the oil from the larval stage showed a phototactic response, as seen in FIG. 5c. Therefore, the oil treatment can prevent the biochemical, structural, and physiological defects caused by the mutation.

Flies were placed in a countercurrent distribution apparatus and responses to light were analyzed. Each numbered tube represents the number of positive responses in a total of 5 trials. In control tests for the from-light response, neither group of flies moved away from light.

The data given above for bubblegum refer to male flies homozygous for the second-chromosome P-element insertion. Homozygous females show the same age-dependent degeneration phenotype, which is similarly prevented by feeding the oil. It was therefore surprising to find that the excess of VLCFAs seen in males was not present in females analyzed by the same procedure. Nor did females show a reduction in lifespan. These aberrations suggest that there might not be a direct causal linkage between the fatty acid anomaly and the bubblegum phenotype, which may, instead, be separate ramifications of an underlying defect, with females being able to compensate for some, but not all, of the consequences. This paradox prompts further inquiry. Whether a similar effect occurs with the X-linked ALD gene in humans is very difficult to determine, since the occurrence of homozygous females is vanishing rare.

What is claimed is:

1. A substantially purified polypeptide comprising the amino acid sequence set forth in SEQ ID NO:2.

2. An isolated polypeptide consisting of the amino acid sequence of SEQ ID NO:2.

3. A method of identifying a compound that inhibits the thioesterification activity of VLCFA coA-syn, the method comprising:
   a) providing a polypeptide comprising the amino acid sequence of SEQ ID NO:2;
   b) contacting the polypeptide with a thioesterifiable substrate and the compound; and
   c) measuring the amount of thioesterification in the presence or absence of the compound, wherein a decrease in thioesterification in the presence of the compound is indicative of a compound that inhibits the thioesterification activity of the polypeptide.

4. A method of identifying a compound that increases the thioesterification activity of VLCFA coA-syn, the method comprising:
   a) providing a polypeptide comprising the amino acid sequence of SEQ ID NO:2;
   b) contacting the polypeptide with a thioesterifiable substrate and determining the amount of thioesterified substrate;
   c) contacting the polypeptide with a thioesterifiable substrate in the presence of the compound and determining the amount of thioesterified substrate; and
   d) comparing the amount of thioesterified substrate obtained in b) with the amount obtained in c), wherein an increase in thioesterified substrate in the presence of the compound is indicative of a compound that increases the thioesterification activity of the polypeptide.

5. The method of claims 3 or 4, wherein the compound is a peptide.

6. The method of claims 3 or 4, wherein the compound is a peptidomimetic.

7. The method of claims 3 or 4, wherein the compound is a small organic compound.

* * * * *

SEQUENCE LISTING

<160> NUMBER OF SEQ ID NOS: 4

<210> SEQ ID NO 1
<211> LENGTH: 2502
<212> TYPE: DNA
<213> ORGANISM: Drosophila melanogaster
<220> FEATURE:
<221> NAME/KEY: CDS
<222> LOCATION: (161)...(2107)

<400> SEQUENCE: 1
ctgaattcgg tcgtgtttgc tgtcgtggtt ctcgagcgaa agaaagagtg ggagtataga      60

-continued

```
aaatagacgg caatcgattt gcgtgaccaa agaacaaata tatacataca tatatcgaga      120
acgccgtaga aacaccaaac tagttaatta tccttgcaac atg tcc acg ata gac       175
                                            Met Ser Thr Ile Asp
                                            1               5 gcg ctc tac aat cgt cct ggg ccc aac cgc ctg cgg cag gcg gat gcc       223
Ala Leu Tyr Asn Arg Pro Gly Pro Asn Arg Leu Arg Gln Ala Asp Ala
            10                  15                  20 tat cgc acc acc aat cgt cag gat gcc gtc aag att cgt atg gcc aag       271
Tyr Arg Thr Thr Asn Arg Gln Asp Ala Val Lys Ile Arg Met Ala Lys
                25                  30                  35 gat gga atc ggc gca gag gag ccc atc tcc gtg ccc ggc ctg ctg aag       319
Asp Gly Ile Gly Ala Glu Glu Pro Ile Ser Val Pro Gly Leu Leu Lys
        40                  45                  50 cgt acg gtc aac aat tat ggc gac tat cct gcg ctg cgc acc aag aac       367
Arg Thr Val Asn Asn Tyr Gly Asp Tyr Pro Ala Leu Arg Thr Lys Asn
    55                  60                  65 ggc aag aac gga tat cac act gtc acc tac aaa caa tat gag cag aag       415
Gly Lys Asn Gly Tyr His Thr Val Thr Tyr Lys Gln Tyr Glu Gln Lys
70                  75                  80                  85 gtg cac cag gtg gcc aag gcg ttc att aag ctc ggt ctg gag gag cac       463
Val His Gln Val Ala Lys Ala Phe Ile Lys Leu Gly Leu Glu Glu His
                90                  95                 100 cat tcg gtg ggt gtg ctg gcc ttc aat tgc gcc gaa tgg ttc tac tcg       511
His Ser Val Gly Val Leu Ala Phe Asn Cys Ala Glu Trp Phe Tyr Ser
            105                 110                 115 gcc atg ggc gcc att cac gca cga ggc atc atc gcc gga atc tac acc       559
Ala Met Gly Ala Ile His Ala Arg Gly Ile Ile Ala Gly Ile Tyr Thr
        120                 125                 130 acc aat tcc gcc gat gca gtg cag cac gtt ctg gag agc tca cat gcc       607
Thr Asn Ser Ala Asp Ala Val Gln His Val Leu Glu Ser Ser His Ala
    135                 140                 145 caa atc gtg gtc gtc gac gac gcc aag caa atg gac aag att cac gcc       655
Gln Ile Val Val Val Asp Asp Ala Lys Gln Met Asp Lys Ile His Ala
150                 155                 160                 165 att cgc gac aag ctg ccc aag ctc aag gcc gcc att cag atc cag gag       703
Ile Arg Asp Lys Leu Pro Lys Leu Lys Ala Ala Ile Gln Ile Gln Glu
                170                 175                 180 ccc tat tcc ccc tac ttg aag aag gag gat ggc tac tac agg tgg tcg       751
Pro Tyr Ser Pro Tyr Leu Lys Lys Glu Asp Gly Tyr Tyr Arg Trp Ser
            185                 190                 195 gag atc gag tcg atg aac gtt agc gac gtg gag gat cag tac atg acc       799
Glu Ile Glu Ser Met Asn Val Ser Asp Val Glu Asp Gln Tyr Met Thr
        200                 205                 210 cgt ttg gag aat gtg gcg atc aac gag tgc tgc tgc ctg gtc tac acc       847
Arg Leu Glu Asn Val Ala Ile Asn Glu Cys Cys Cys Leu Val Tyr Thr
    215                 220                 225 tcc gga acg gtg ggc atg ccc aag ggc gtg atg ctc tcc cac gac aac       895
Ser Gly Thr Val Gly Met Pro Lys Gly Val Met Leu Ser His Asp Asn
230                 235                 240                 245 atc acc ttc gat gtg cgc ggc atc gtc aag gcc atg gac cgt gtg gtg       943
Ile Thr Phe Asp Val Arg Gly Ile Val Lys Ala Met Asp Arg Val Val
                250                 255                 260 gtt ggg gcg gag tcg atc gtc tcc tac ctg cca ctt tcg cac gtg gcc       991
Val Gly Ala Glu Ser Ile Val Ser Tyr Leu Pro Leu Ser His Val Ala
            265                 270                 275 gcc cag acc gtg gac att tac acc tgc gcc ttt gtg gcg ggc tgc att      1039
Ala Gln Thr Val Asp Ile Tyr Thr Cys Ala Phe Val Ala Gly Cys Ile
        280                 285                 290 tgg ttc gcc gac aag gat gcg ctg aag gga acg ctg gtg aag tcg ttg      1087
```

```
Trp Phe Ala Asp Lys Asp Ala Leu Lys Gly Thr Leu Val Lys Ser Leu
    295                 300                 305 cag gat gcg cga ccc acg cga ttc atg ggc gtg ccg cgt gtg tac gag      1135
Gln Asp Ala Arg Pro Thr Arg Phe Met Gly Val Pro Arg Val Tyr Glu
310                 315                 320                 325 aag ttc cag gag cga atg gtc gcc gtg gcc agc tcc agc ggc agc ctg      1183
Lys Phe Gln Glu Arg Met Val Ala Val Ala Ser Ser Ser Gly Ser Leu
                330                 335                 340 aag aag atg ctc gcc agc tgg gcc aag ggc atc acg ctg aag cac tac      1231
Lys Lys Met Leu Ala Ser Trp Ala Lys Gly Ile Thr Leu Lys His Tyr
            345                 350                 355 atg gtg agt caa ggc aag agc tcc ggg gga ttc cgg tac aag att gcc      1279
Met Val Ser Gln Gly Lys Ser Ser Gly Gly Phe Arg Tyr Lys Ile Ala
        360                 365                 370 aag tcg ctc atc atg tcc aag gtg aag cag gcc ctg ggc ttc gat cgc      1327
Lys Ser Leu Ile Met Ser Lys Val Lys Gln Ala Leu Gly Phe Asp Arg
    375                 380                 385 gtc ctt aca ctg gcc agt gcg gca gct ccc atg tcg ccg gag acg aag      1375
Val Leu Thr Leu Ala Ser Ala Ala Ala Pro Met Ser Pro Glu Thr Lys
390                 395                 400                 405 aag tac ttc ctc agt ctg gac cta aag att gtc gat gcc ttc ggc atg      1423
Lys Tyr Phe Leu Ser Leu Asp Leu Lys Ile Val Asp Ala Phe Gly Met
                410                 415                 420 tca gaa acg gcc ggt tgt cac acc atc tgc ctt ccc gat tcc gtg ggt      1471
Ser Glu Thr Ala Gly Cys His Thr Ile Cys Leu Pro Asp Ser Val Gly
            425                 430                 435 ctg aac aca atc ggc aaa act ttg ccc ggc tgc gag tcc aag ttc atc      1519
Leu Asn Thr Ile Gly Lys Thr Leu Pro Gly Cys Glu Ser Lys Phe Ile
        440                 445                 450 aac aag gat gcc aac ggt cac gga gag ctg tgc atc cga gga cgt cac      1567
Asn Lys Asp Ala Asn Gly His Gly Glu Leu Cys Ile Arg Gly Arg His
    455                 460                 465 gtt ttc atg ggc tac atc gac aac aag gag aag acc gag gag tcg ctg      1615
Val Phe Met Gly Tyr Ile Asp Asn Lys Glu Lys Thr Glu Glu Ser Leu
470                 475                 480                 485 gat gac gac tgc tgg ctg cat tcc ggt gat ttg gga ttt gtg gat gac      1663
Asp Asp Asp Cys Trp Leu His Ser Gly Asp Leu Gly Phe Val Asp Asp
                490                 495                 500 aag ggt tat gtt tca ctg acg gga cga tcc aag gag atc atc att acc      1711
Lys Gly Tyr Val Ser Leu Thr Gly Arg Ser Lys Glu Ile Ile Ile Thr
            505                 510                 515 gcc ggc ggc gag aac ata ccg cca gtg cac atc gag aac acg atc aag      1759
Ala Gly Gly Glu Asn Ile Pro Pro Val His Ile Glu Asn Thr Ile Lys
        520                 525                 530 aag gag ctg gat gcc att tcc aat gcc ttt ttg gtg ggc gag cag cgc      1807
Lys Glu Leu Asp Ala Ile Ser Asn Ala Phe Leu Val Gly Glu Gln Arg
    535                 540                 545 aaa tat ctc act gtt ctg atc acc cta aag acc gaa gtg gac aag gat      1855
Lys Tyr Leu Thr Val Leu Ile Thr Leu Lys Thr Glu Val Asp Lys Asp
550                 555                 560                 565 tcc ggt gag ccg ctg gac gag ctt agc cac gag tcc tcc gtg tgg gtg      1903
Ser Gly Glu Pro Leu Asp Glu Leu Ser His Glu Ser Ser Val Trp Val
                570                 575                 580 aaa tcg ctg gga gtg gag cac aag acc gta tcg gat atc ctg gcc gca      1951
Lys Ser Leu Gly Val Glu His Lys Thr Val Ser Asp Ile Leu Ala Ala
            585                 590                 595 ggt ccc tgc ccc aag gtg tgg aag tcc atc gag gat gcc att aag cgg      1999
Gly Pro Cys Pro Lys Val Trp Lys Ser Ile Glu Asp Ala Ile Lys Arg
        600                 605                 610
```

-continued

| | | | | | | | | | | | | |
|---|---|---|---|---|---|---|---|---|---|---|---|---|
| gcc | aac | aag | cag | tcc | att | tcc | aat | gcc | caa | aag | gtt | cag | aag | ttc | acc | 2047 |
| Ala | Asn | Lys | Gln | Ser | Ile | Ser | Asn | Ala | Gln | Lys | Val | Gln | Lys | Phe | Thr | |
| | 615 | | | | 620 | | | | | 625 | | | | | | |
| att | ctg | ccg | cac | gac | ttc | tcc | att | ccc | acc | ggc | gaa | ctt | gga | ccc | acc | 2095 |
| Ile | Leu | Pro | His | Asp | Phe | Ser | Ile | Pro | Thr | Gly | Glu | Leu | Gly | Pro | Thr | |
| 630 | | | | | 635 | | | | | 640 | | | | | 645 | |
| cac | cct | aaa | ggt | taagcgcaac | gttgtgtcca | agatgtatgc | cgatgagatc | | | | | | | | | 2147 |
| His | Pro | Lys | Gly | | | | | | | | | | | | | | gagaaactat atgcctagat ttctcactgc aagatcgaaa ccgatgatag ccgcggaact   2207
tgagctttaa tgtgaatttg aatttaacgg acttccaagc caattgagtg ccacttttaa   2267
tttgatttag gctgatgtta actgttggat attaaactaa gaacaactat ggccctatgc   2327
ctaggtagac acgagcttgc caacgattag gtccagagat catttaatta gtaactaagt   2387
tttattttt atatactatt tggttgtacc aactgaacaa cgaaaattg tttattgtct   2447
gaagagcaac aataaatttg taattagatt aactaccaaa aaaaaaaaaa aaaaa        2502

<210> SEQ ID NO 2
<211> LENGTH: 649
<212> TYPE: PRT
<213> ORGANISM: Drosophila melanogaster

<400> SEQUENCE: 2

Met Ser Thr Ile Asp Ala Leu Tyr Asn Arg Pro Gly Pro Asn Arg Leu
1               5                   10                  15

Arg Gln Ala Asp Ala Tyr Arg Thr Thr Asn Arg Gln Asp Ala Val Lys
            20                  25                  30

Ile Arg Met Ala Lys Asp Gly Ile Gly Ala Glu Glu Pro Ile Ser Val
        35                  40                  45

Pro Gly Leu Leu Lys Arg Thr Val Asn Asn Tyr Gly Asp Tyr Pro Ala
    50                  55                  60

Leu Arg Thr Lys Asn Gly Lys Asn Gly Tyr His Thr Val Thr Tyr Lys
65                  70                  75                  80

Gln Tyr Glu Gln Lys Val His Gln Val Ala Lys Ala Phe Ile Lys Leu
                85                  90                  95

Gly Leu Glu Glu His His Ser Val Gly Val Leu Ala Phe Asn Cys Ala
            100                 105                 110

Glu Trp Phe Tyr Ser Ala Met Gly Ala Ile His Ala Arg Gly Ile Ile
        115                 120                 125

Ala Gly Ile Tyr Thr Thr Asn Ser Ala Asp Ala Val Gln His Val Leu
    130                 135                 140

Glu Ser Ser His Ala Gln Ile Val Val Asp Asp Ala Lys Gln Met
145                 150                 155                 160

Asp Lys Ile His Ala Ile Arg Asp Lys Leu Pro Lys Leu Lys Ala Ala
                165                 170                 175

Ile Gln Ile Gln Glu Pro Tyr Ser Pro Tyr Leu Lys Lys Glu Asp Gly
            180                 185                 190

Tyr Tyr Arg Trp Ser Glu Ile Glu Ser Met Asn Val Ser Asp Val Glu
        195                 200                 205

Asp Gln Tyr Met Thr Arg Leu Glu Asn Val Ala Ile Asn Glu Cys Cys
    210                 215                 220

Cys Leu Val Tyr Thr Ser Gly Thr Val Gly Met Pro Lys Gly Val Met
225                 230                 235                 240

Leu Ser His Asp Asn Ile Thr Phe Asp Val Arg Gly Ile Val Lys Ala
                245                 250                 255

-continued

Met Asp Arg Val Val Gly Ala Glu Ser Ile Val Ser Tyr Leu Pro
         260                 265                 270

Leu Ser His Val Ala Ala Gln Thr Val Asp Ile Tyr Thr Cys Ala Phe
         275                 280                 285

Val Ala Gly Cys Ile Trp Phe Ala Asp Lys Asp Ala Leu Lys Gly Thr
290                 295                 300

Leu Val Lys Ser Leu Gln Asp Ala Arg Pro Thr Arg Phe Met Gly Val
305                 310                 315                 320

Pro Arg Val Tyr Glu Lys Phe Gln Glu Arg Met Val Ala Val Ala Ser
                 325                 330                 335

Ser Ser Gly Ser Leu Lys Lys Met Leu Ala Ser Trp Ala Lys Gly Ile
             340                 345                 350

Thr Leu Lys His Tyr Met Val Ser Gln Gly Lys Ser Ser Gly Gly Phe
             355                 360                 365

Arg Tyr Lys Ile Ala Lys Ser Leu Ile Met Ser Lys Val Lys Gln Ala
370                 375                 380

Leu Gly Phe Asp Arg Val Leu Thr Leu Ala Ser Ala Ala Ala Pro Met
385                 390                 395                 400

Ser Pro Glu Thr Lys Lys Tyr Phe Leu Ser Leu Asp Leu Lys Ile Val
                 405                 410                 415

Asp Ala Phe Gly Met Ser Glu Thr Ala Gly Cys His Thr Ile Cys Leu
             420                 425                 430

Pro Asp Ser Val Gly Leu Asn Thr Ile Gly Lys Thr Leu Pro Gly Cys
             435                 440                 445

Glu Ser Lys Phe Ile Asn Lys Asp Ala Asn Gly His Gly Glu Leu Cys
         450                 455                 460

Ile Arg Gly Arg His Val Phe Met Gly Tyr Ile Asp Asn Lys Glu Lys
465                 470                 475                 480

Thr Glu Glu Ser Leu Asp Asp Asp Cys Trp Leu His Ser Gly Asp Leu
                 485                 490                 495

Gly Phe Val Asp Asp Lys Gly Tyr Val Ser Leu Thr Gly Arg Ser Lys
             500                 505                 510

Glu Ile Ile Ile Thr Ala Gly Gly Glu Asn Ile Pro Pro Val His Ile
         515                 520                 525

Glu Asn Thr Ile Lys Lys Glu Leu Asp Ala Ile Ser Asn Ala Phe Leu
         530                 535                 540

Val Gly Glu Gln Arg Lys Tyr Leu Thr Val Leu Ile Thr Leu Lys Thr
545                 550                 555                 560

Glu Val Asp Lys Asp Ser Gly Glu Pro Leu Asp Glu Leu Ser His Glu
                 565                 570                 575

Ser Ser Val Trp Val Lys Ser Leu Gly Val Glu His Lys Thr Val Ser
             580                 585                 590

Asp Ile Leu Ala Ala Gly Pro Cys Pro Lys Val Trp Lys Ser Ile Glu
         595                 600                 605

Asp Ala Ile Lys Arg Ala Asn Lys Gln Ser Ile Ser Asn Ala Gln Lys
         610                 615                 620

Val Gln Lys Phe Thr Ile Leu Pro His Asp Phe Ser Ile Pro Thr Gly
625                 630                 635                 640

Glu Leu Gly Pro Thr His Pro Lys Gly
                 645

<210> SEQ ID NO 3
<211> LENGTH: 634
<212> TYPE: PRT

<213> ORGANISM: Homo sapiens

<400> SEQUENCE: 3

```
Arg Leu Arg Ile Asp Pro Ser Cys Pro Gln Leu Pro Tyr Thr Val His
  1               5                  10                  15

Arg Met Phe Tyr Glu Ala Leu Asp Lys Tyr Gly Asp Leu Ile Ala Leu
             20                  25                  30

Gly Phe Lys Arg Gln Asp Lys Trp Glu His Ile Ser Tyr Ser Gln Tyr
         35                  40                  45

Tyr Leu Leu Ala Arg Arg Ala Lys Gly Phe Leu Lys Leu Gly Leu
 50                  55                  60

Lys Gln Ala His Ser Val Ala Ile Leu Gly Phe Asn Ser Pro Glu Trp
 65                  70                  75                  80

Phe Phe Ser Ala Val Gly Thr Val Phe Ala Gly Gly Ile Val Thr Gly
                 85                  90                  95

Ile Tyr Thr Thr Ser Ser Pro Glu Ala Cys Gln Tyr Ile Ala Tyr Asp
                100                 105                 110

Cys Cys Ala Asn Val Ile Met Val Asp Thr Gln Lys Gln Leu Glu Lys
            115                 120                 125

Ile Leu Lys Ile Trp Lys Gln Leu Pro His Leu Lys Ala Val Val Ile
130                 135                 140

Tyr Lys Glu Pro Pro Pro Asn Lys Met Ala Asn Val Tyr Thr Met Glu
145                 150                 155                 160

Glu Phe Met Glu Leu Gly Asn Glu Val Pro Glu Glu Ala Leu Asp Ala
                165                 170                 175

Ile Ile Asp Thr Gln Gln Pro Asn Gln Cys Cys Val Leu Val Tyr Thr
            180                 185                 190

Ser Gly Thr Thr Gly Asn Pro Lys Gly Val Met Leu Ser Gln Asp Asn
        195                 200                 205

Ile Thr Trp Thr Ala Arg Tyr Gly Ser Gln Ala Gly Asp Ile Arg Pro
210                 215                 220

Ala Glu Val Gln Gln Glu Val Val Ser Tyr Leu Pro Leu Ser His
225                 230                 235                 240

Ile Ala Ala Gln Ile Tyr Asp Leu Trp Thr Gly Ile Gln Trp Gly Ala
                245                 250                 255

Gln Val Cys Phe Ala Glu Pro Asp Ala Leu Lys Gly Ser Leu Val Asn
            260                 265                 270

Thr Leu Arg Glu Val Glu Pro Ser His Met Gly Val Pro Arg Val
        275                 280                 285

Trp Glu Lys Ile Met Glu Arg Ile Gln Glu Val Ala Ala Gln Ser Gly
290                 295                 300

Phe Ile Arg Arg Lys Met Leu Leu Trp Ala Met Ser Val Thr Leu Glu
305                 310                 315                 320

Gln Asn Leu Thr Cys Pro Gly Ser Asp Leu Lys Pro Phe Thr Thr Arg
                325                 330                 335

Leu Ala Asp Tyr Leu Val Leu Ala Lys Val Arg Gln Ala Leu Gly Phe
            340                 345                 350

Ala Lys Cys Gln Lys Asn Phe Tyr Gly Ala Ala Pro Met Met Ala Glu
        355                 360                 365

Thr Gln His Phe Phe Leu Gly Leu Asn Ile Arg Leu Tyr Ala Gly Tyr
370                 375                 380

Gly Leu Ser Glu Thr Ser Gly Pro His Phe Met Ser Ser Pro Tyr Asn
385                 390                 395                 400
```

```
Tyr Arg Leu Tyr Ser Ser Gly Lys Leu Val Pro Gly Cys Arg Val Lys
                405                 410                 415

Leu Val Asn Gln Asp Ala Glu Gly Ile Gly Glu Ile Cys Leu Trp Gly
            420                 425                 430

Arg Thr Ile Phe Met Gly Tyr Leu Asn Met Glu Asp Lys Thr Cys Glu
        435                 440                 445

Ala Ile Asp Glu Glu Gly Trp Leu His Thr Gly Asp Ala Gly Arg Leu
450                 455                 460

Asp Ala Asp Gly Phe Leu Tyr Ile Thr Gly Arg Leu Lys Glu Leu Ile
465                 470                 475                 480

Ile Thr Ala Gly Gly Glu Asn Val Pro Pro Val Pro Ile Glu Glu Ala
                485                 490                 495

Val Lys Met Glu Leu Pro Ile Ile Ser Asn Ala Met Leu Ile Gly Asp
            500                 505                 510

Gln Arg Lys Phe Leu Ser Met Leu Leu Thr Leu Lys Cys Thr Leu Asp
        515                 520                 525

Pro Asp Thr Ser Asp Gln Thr Asp Asn Leu Thr Glu Gln Ala Val Glu
530                 535                 540

Phe Cys Gln Arg Val Gly Ser Arg Ala Thr Thr Val Ser Glu Ile Ile
545                 550                 555                 560

Glu Lys Lys Asp Glu Ala Val Tyr Gln Ala Ile Glu Glu Gly Ile Arg
                565                 570                 575

Arg Val Asn Met Asn Ala Ala Ala Arg Pro Tyr His Ile Gln Lys Trp
            580                 585                 590

Ala Ile Leu Glu Arg Asp Phe Ser Ile Ser Gly Gly Glu Leu Gly Pro
        595                 600                 605

Thr Met Lys Leu Lys Arg Leu Thr Val Leu Glu Lys Tyr Lys Gly Ile
    610                 615                 620

Ile Asp Ser Phe Tyr Gln Glu Gln Lys Met
625                 630

<210> SEQ ID NO 4
<211> LENGTH: 620
<212> TYPE: PRT
<213> ORGANISM: Rattus norvegicus

<400> SEQUENCE: 4

Met Leu Pro Val Leu Tyr Thr Gly Leu Ala Gly Leu Leu Leu Leu Pro
1               5                   10                  15

Leu Leu Leu Thr Cys Cys Pro Tyr Leu Leu Gln Asp Val Arg Phe
            20                  25                  30

Phe Leu Gln Leu Ala Asn Met Ala Arg Gln Val Arg Ser Tyr Arg Gln
        35                  40                  45

Arg Arg Pro Val Arg Thr Ile Leu His Val Phe Leu Glu Gln Ala Arg
    50                  55                  60

Lys Thr Pro His Lys Pro Phe Leu Leu Phe Arg Asp Glu Thr Leu Thr
65                  70                  75                  80

Tyr Ala Gln Val Asp Arg Arg Ser Asn Gln Val Ala Arg Ala Leu His
                85                  90                  95

Asp His Leu Gly Leu Arg Gln Gly Asp Cys Val Ala Leu Phe Met Gly
            100                 105                 110

Asn Glu Pro Ala Tyr Val Trp Leu Trp Leu Gly Leu Leu Lys Leu Gly
        115                 120                 125

Cys Pro Met Ala Cys Leu Asn Tyr Asn Ile Arg Ala Lys Ser Leu Leu
    130                 135                 140
```

-continued

```
His Cys Phe Gln Cys Cys Gly Ala Lys Val Leu Leu Ala Ser Pro Glu
145                 150                 155                 160

Leu His Glu Ala Val Glu Val Leu Pro Thr Leu Lys Lys Glu Gly
                165                 170                 175

Val Ser Val Phe Tyr Val Ser Arg Thr Ser Asn Thr Asn Gly Val Asp
                180                 185                 190

Thr Val Leu Asp Lys Val Asp Gly Val Ser Ala Asp Pro Ile Pro Glu
                195                 200                 205

Ser Trp Arg Ser Glu Val Thr Phe Thr Thr Pro Ala Val Tyr Ile Tyr
210                 215                 220

Thr Ser Gly Thr Thr Gly Leu Pro Lys Ala Ala Thr Ile Asn His His
225                 230                 235                 240

Arg Leu Trp Tyr Gly Thr Ser Leu Ala Leu Arg Ser Gly Ile Lys Ala
                245                 250                 255

His Asp Val Ile Tyr Thr Thr Met Pro Leu Tyr His Ser Ala Ala Leu
                260                 265                 270

Met Ile Gly Leu His Gly Cys Ile Val Val Gly Ala Thr Phe Ala Leu
                275                 280                 285

Arg Ser Lys Phe Ser Ala Ser Gln Phe Trp Asp Asp Cys Arg Lys Tyr
290                 295                 300

Asn Ala Thr Val Ile Gln Tyr Ile Gly Glu Leu Leu Arg Tyr Leu Cys
305                 310                 315                 320

Asn Thr Pro Gln Lys Pro Asn Asp Arg Asp His Lys Val Lys Ile Ala
                325                 330                 335

Leu Gly Asn Gly Leu Arg Gly Asp Val Trp Arg Glu Phe Ile Lys Arg
                340                 345                 350

Phe Gly Asp Ile His Ile Tyr Glu Phe Tyr Ala Ser Thr Glu Gly Asn
                355                 360                 365

Ile Gly Phe Met Asn Tyr Pro Arg Lys Ile Gly Ala Val Gly Arg Glu
370                 375                 380

Asn Tyr Leu Gln Lys Lys Val Val Arg His Glu Leu Ile Lys Tyr Asp
385                 390                 395                 400

Val Glu Lys Asp Glu Pro Val Arg Asp Ala Asn Gly Tyr Cys Ile Lys
                405                 410                 415

Val Pro Lys Gly Glu Val Gly Leu Leu Ile Cys Lys Ile Thr Glu Leu
                420                 425                 430

Thr Pro Phe Phe Gly Tyr Ala Gly Gly Lys Thr Gln Thr Glu Lys Lys
                435                 440                 445

Lys Leu Arg Asp Val Phe Lys Lys Gly Asp Val Tyr Phe Asn Ser Gly
450                 455                 460

Asp Leu Leu Met Ile Asp Arg Glu Asn Phe Ile Tyr Phe His Asp Arg
465                 470                 475                 480

Val Gly Asp Thr Phe Arg Trp Lys Gly Glu Asn Val Ala Thr Thr Glu
                485                 490                 495

Val Ala Asp Ile Val Gly Leu Val Asp Phe Val Glu Glu Val Asn Val
                500                 505                 510

Tyr Gly Val Pro Val Pro Gly His Glu Gly Arg Ile Gly Met Ala Ser
                515                 520                 525

Ile Lys Met Lys Glu Asn Tyr Glu Phe Asn Gly Lys Lys Leu Phe Gln
530                 535                 540

His Ile Ser Glu Tyr Leu Pro Ser Tyr Ser Arg Pro Arg Phe Leu Arg
545                 550                 555                 560
```

-continued

```
Ile Gln Asp Thr Ile Glu Ile Thr Gly Thr Phe Lys His Arg Lys Val
            565             570             575

Thr Leu Met Glu Glu Gly Phe Asn Pro Ser Val Ile Lys Asp Thr Leu
            580             585             590

Tyr Phe Met Asp Asp Thr Glu Lys Thr Tyr Val Pro Met Thr Glu Asp
            595             600             605

Ile Tyr Asn Ala Ile Ile Asp Lys Thr Leu Lys Leu
            610             615             620
```